(12) United States Patent
Chinnadurai

(10) Patent No.: US 6,716,964 B1
(45) Date of Patent: Apr. 6, 2004

(54) CTIP, A NOVEL PROTEIN THAT INTERACTS WITH CTBP AND USES THEREFOR

(75) Inventor: Govindaswamy Chinnadurai, St. Louis, MO (US)

(73) Assignee: Saint Louis University, St. Louis, MO (US)

( * ) Notice: Subject to any disclaimer, the term of this patent is extended or adjusted under 35 U.S.C. 154(b) by 0 days.

(21) Appl. No.: 09/581,094

(22) PCT Filed: Dec. 11, 1998

(86) PCT No.: PCT/US98/26505

§ 371 (c)(1),
(2), (4) Date: Aug. 18, 2000

(87) PCT Pub. No.: WO99/29334

PCT Pub. Date: Jun. 17, 1999

Related U.S. Application Data

(60) Provisional application No. 60/069,362, filed on Dec. 12, 1997.

(51) Int. Cl.[7] .............................. C07K 1/00; C07K 2/00; C07K 4/00; C07K 14/00; C07K 17/00
(52) U.S. Cl. ....................... 530/350; 530/300; 435/69.1
(58) Field of Search ................................ 530/300, 350; 435/69.1

(56) References Cited

U.S. PATENT DOCUMENTS 6,030,832 A * 2/2000 Wong et al.

FOREIGN PATENT DOCUMENTS

| WO | WO 92/20803 | * 11/1992 |
| WO | WO 97/06250 | * 2/1997 |

OTHER PUBLICATIONS

GemCore amino acid database sheet. Sequence alignment between Applicants' SEQ ID NO:2 and sequence 6 of U.S. Patent No. 6,030,832. Feb. 2000.*
GenCore amino acid database sheet. Sequence alignment between Applicants' SEQ ID NO: 2 and sequence from J. Biol. Chem. paper, Apr. 10, 1998.*
GenCore database, amino acid database comparison. Accession No. AAR29175 from WO 9220803, Nov. 26, 1992.*
GenCore database, amino acid database comparison. Accession No. AAT66337 from WO 9706250, Feb. 20, 1997.*
Dyson et al., Adenovirus E1A targets key regulators of cell proliferation, *Cancer Surv* 12:161–95, 1992.
Nevins, E2F: a link between the Rb tumor suppressor protein and viral oncoproteins; *Science* 258: 424–429, 1992.
Moran, DNA tumor virus transforming proteins and the cell cycle, *Current Opinion in Genetics and Development*, 3:63–70, 1993.

Mymryk et al., Multiple pathways for gene activation in rodent cells by the smaller adenovirus 5 E1A protein and their relevance to growth and transformation, *J. Gen. Virol* 74, 2131–2141, 1993.
Yang et al., A p300/CBP–associated factor that competes with the adenoviral oncoprotein E1A, *Nature* 382; 319–324, 1996.
Mymryk et al., Induction of gene expression by exon 2 of the major E1A proteins of adenovirus type 5, *J. Virol.* 67, 6922–6928, 1993.
Subramanian et al., Enhanced ras oncogene mediated cell transformation and tumorigenesis by adenovirus 2 mutants lacking the C–terminal region of E1a protein, *Oncogene* 4:415–520, 1989.
Quinlan et al., Immortalization of primary epithelial cells requires first– and second–exon functions of adenovirus type 5 12S, *J. Virol.* 66:2020–2030, 1992.
Urbanelli et al., C–terminal domain of the adenovirus E1A oncogene product is required for induction of cytotoxic T lymphocytes and tumor–specific transplantation immunity, *Virol.* 173:607–614, 1989.
Douglas et al., Modulation of transformation of primary epithelial cells by the second exon of the Ad5 E1A12S gene, *Oncogene* 6:2093–2103, 1991.
Pozzatti et al., Primary rat embryo cells transformed by one or two oncogenes show different metastic potentials, *Science* 232:223–227, 1986.
Pozzatti et al. The E1a gene of adenovirus type 2 reduces the metastic potential of ras–transformed rat embryo cells, *Mol. Cell Biol*, 8(7):2984–2988, 1988.
Steeg et al., Alteref expression of NM23, a gene associated with low tumor metastic potential, during adenovirus 2 E1a inhibition of experimental metastasis, *Cancer Res.* 48:6550–6554, 1988.
Boyd et al., A region in the C–terminus of adenovirus 2/5 E1a protein is required for association with a cellular phosphoprotein and important for the negative modulation of T24–ras mediated transformation, tumorigenesis and metastasis, *EMBO J*. 12:469–478, 1993.
Schaeper et al., Molecular cloning and characterization of a cellular phosphoprotein that interacts with a conserved C–terminal domain of adenovirus E1A involved in negative modulation of oncogenic transformation, *Proc. Natl. Acad. Sci. USA* 92:10467–10471, 1995.

(List continued on next page.)

*Primary Examiner*—Alana M. Harris

(57) ABSTRACT

A novel human protein, CtIP, that interacts with the human cellular protein CtBP, and the nucleotide sequence encoding CtIP are provided. CtIP is useful in diagnostic methods for determining malignancy of cells and in methods for inhibiting neoplasia in patients. Use of CtIP in a method for identifying agents that can inhibit neoplasia of cells is also disclosed.

2 Claims, 11 Drawing Sheets

OTHER PUBLICATIONS

Schaeper et al., Interaction between a cellular protein the binds to the C-terminal region of adenovirus E1A (CtBP) and a novel cellular protein is disrupted by E1A thrugh a conserved PLDLS motif, *J. Biol. Chem.* 273:8549–8552, 1998.

Sollerbrant et al., The CtBP binding domain in the adenovirus E1A protein controls CR1-dependent transactivation. *Nucl. Acids. Res.*, 24:2578–2584, 1996.

Hobohm et al., A sequence property approach to searching protein databases, *J. Mol. Biol.* 251:390–399, 1995.

Durfee et al., The retinoblastoma protein associates with the protein phosphatase type 1 catalytic subunit, *Genes Dev.* 7:555–569, 1993.

Chien et al., The two-hybrid system: a method to identify and clone genes for proteins that interact with a protein of interest, *Proc. Natl. Acad. Sci. USA* 88:9578–9582, 1991.

* cited by examiner

```
   1 cgggtccggc cgctccgagc ccggccgcag cccccggctt aaagcgcggg ctgtccggag
  61 ggtcggcttt cccaccgagg atttggcact ctggtgaggg ttttgggcga aagagaaaag
 121 cgagcagccg tccttcacag cctcagaaag tgctcgcttc ccttcggggc tttcgcgaat
 181 cccgaggcaa tctcggaggc ggtatttgac ctgtccaaag acgacttgat acctctataa
 241 tgtaacagaa aaggtcagaa aatattaagc aagtagaagt gtggagcata ttaagcaaga
 301 tgaacatctt gggaagcagc tgtggaagcc ctaactctgc agatacatct agtgacttta
 361 aggacctttg gacaaaacta aaagaatgtc atgatagaga agtacaaggt ttacaagtaa
 421 aagtaaccaa gctaaaacag gaacgaatct tagatgcaca aagactagaa gaattcttca
 481 ccaaaaatca acagctgagg gaacagcaga aagtccttca tgaaaccatt aaagttttag
 541 aagatcggtt aagagcaggc ttatgtgatc gctgtgcagt aactgaagaa catatgcgga
 601 aaaaacagca agagtttgaa aatatccggc agcagaatct taaacttatt acagaactta
 661 tgaatgaaag gaatactcta caggaagaaa ataaaaagct ttctgaacaa ctccagcaga
 721 aaattgagaa tgatcaacag catcaagcag ctgagcttga atgtgaggaa gacgttattc
 781 cagattcacc gataacagcc ttctcatttt ctggcgttaa ccggctacga agaaaggaga
 841 accccccatgt ccgatacata gaacaaacac atactaaatt ggagcactct gtgtgtgcaa
 901 atgaaatgag aaaagtttcc aagtcttcaa ctcatccaca acataatcct aatgaaaatg
 961 aaattctagt agctgacact tatgaccaaa gtcaatcctc aatggccaaa gcacatggaa
1021 caagcagcta tacccctgat aagtcatctt ttaatttagc tacagttgtt gctgaaacac
1081 ttggacttgg tgttcaagaa gaatctgaaa ctcaaggtcc catgagcccc cttggtgatg
1141 agctctacca ctgtctggaa ggaaatcaca agaaacagcc ttttgaggaa tctacaagaa
1201 atactgaaga tagtttaaga ttttcagatt ctacttcaaa gactcctcct caagaagaat
1261 tacctactcg agtgtcatct cctgtatttg gagctacctc tagtatcaaa agtggtttag
1321 atttgaatac aagtttgtcc ccttctcttt tacagcctgg gaaaaaaaaa catctgaaaa
1381 cactcccttt tagcaacact tgtatatcta gattagaaaa aactagatca aaatctgaag
1441 atagtgccct tttcacacat cacagtcttg ggtctgaagt gaacaagatc attatccagt
1501 catctaataa acagatactt ataaataaaa atataagtga atccctaggt gaacagaata
1561 ggactgagta cggtaaagat tctaacactg ataaacattt ggagccctg aaatcattgg
1621 gaggccgaac atccaaaagg aagaaaactg aggaagaaag tgaacatgaa gtaagctgcc
1681 cccaagcttc ttttgataaa gaaaatgctt tccctttcc aatggataat cagttttcca
1741 tgaatggaga ctgtgtgatg gataaacctc tggatctgtc tgatcgattt tcagctattc
1801 agcgtcaaga gaaaagccaa ggaagtgaga cttctaaaaa caaatttagg caagtgactc
1861 tttatgaggc tttgaagacc attccaaagg gctttccctc aagccgtaag gcctcagatg
1921 gcaactgcac gttgcccaaa gattcccag gggagccctg ttcacaggaa tgcatcatcc
1981 ttcagccctt gaataaatgc tctccagaca ataaaccatc attacaaata aagaagaaa
2041 atgctgtctt taaaattcct ctacgtccac gtgaaagttt ggagactgag aatgttttag
2101 atgacataaa gagtgctggt tctcatgagc caataaaaat acaaaccagg tcagaccatg
2161 gaggatgtga acttgcatca gttcttcagt taaatccatg tagaactggt aaaataaagt
2221 ctctacaaaa caaccaagat gtatcctttg aaaatatcca gtggagtata gatccgggag
2281 cagaccttc tcagtataaa atggatgtta ctgtaataga tacaaaggat ggcagtcagt
2341 caaaattagg aggagagaca gtggacatgg actgtacatt ggttagtgaa accgttctct
2401 taaaaatgaa gaagcaagag cagaagggag aaaaaagttc aaatgaagaa agaaaaatga
2461 atgatagctt ggaagatatg tttgatcgga caacacatga agagtatgaa tcctgtttgg
2521 cagacagttt ctcccaagca gcagatgaag aggaggaatt gtctactgcc acaaagaaac
2581 tacacactca tggtgataaa caagacaaag tcaagcagaa agcgtttgtg gagccgtatt
2641 ttaaggtga tgaaagagag actagcttgc aaaattttcc tcatattgag gtggttcgga
2701 aaaaagagga gagaagaaaa ctgcttgggc acacgtgtaa ggaatgtgaa atttattatg
2761 cagatatgcc agcagaagaa agagaaaaga aattggcttc ctgctcaaga caccgattcc
2821 gctacattcc acccaacaca ccagagaatt tttgggaagt tggttttcct tccactcaga
2881 cttgtatgga aagaggttat attaaggaag atcttgatcc ttgtcctcgt ccaaaaagac
2941 gtcagcctta caacgcaata ttttctccaa aaggcaagga gcagaagaca tagacgttga
3001 aacagaaaca gaaggatgaa ggacagtttt ttccttctta gttatttata gttaaagttg
3061 gtactaaaca ttgattttt tgatcttctg taaatggatt tataatcag ttttctattg
3121 aaaatgtttg tgatattttg cttttgcacc tttaaaacaa taaggcgctt tcatttttgca
3181 ctctaactta agagttttta ctttatgtag tgatacctaa tacaatttg aaaatacaaa
3241 aaaaaaa
```

Figure 2A

```
            10         20         30         40         50         60
            |          |          |          |          |          |
  1 ATGAACATCT TGGGAAGCAG CTGTGGAAGC CCTAACTCTG CAGATACATC TAGTGACTTT
    TACTTGTAGA ACCCTTCGTC GACACCTTCG GGATTGAGAC GTCTATGTAG ATCACTGAAA

61 AAGGACCTTT GGACAAAACT AAAAGAATGT CATGATAGAG AAGTACAAGG TTTACAAGTA
    TTCCTGGAAA CCTGTTTTGA TTTTCTTACA GTACTATCTC TTCATGTTCC AAATGTTCAT

121 AAAGTAACCA AGCTAAAACA GGAACGAATC TTAGATGCAC AAAGACTAGA AGAATTCTTC
    TTTCATTGGT TCGATTTTGT CCTTGCTTAG AATCTACGTG TTTCTGATCT TCTTAAGAAG

181 ACCAAAAATC AACAGCTGAG GGAACAGCAG AAAGTCCTTC ATGAAACCAT TAAAGTTTTA
    TGGTTTTTAG TTGTCGACTC CCTTGTCGTC TTTCAGGAAG TACTTTGGTA ATTTCAAAAT

241 GAAGATCGGT TAAGAGCAGG CTTATGTGAT CGCTGTGCAG TAACTGAAGA ACATATGCGG
    CTTCTAGCCA ATTCTCGTCC GAATACACTA GCGACACGTC ATTGACTTCT TGTATACGCC

301 AAAAAACAGC AAGAGTTTGA AAATATCCGG CAGCAGAATC TTAAACTTAT TACAGAACTT
    TTTTTTGTCG TTCTCAAACT TTTATAGGCC GTCGTCTTAG AATTTGAATA ATGTCTTGAA

361 ATGAATGAAA GGAATACTCT ACAGGAAGAA AATAAAAAGC TTTCTGAACA ACTCCAGCAG
    TACTTACTTT CCTTATGAGA TGTCCTTCTT TTATTTTTCG AAAGACTTGT TGAGGTCGTC

421 AAAATTGAGA ATGATCAACA GCATCAAGCA GCTGAGCTTG AATGTGAGGA AGACGTTATT
    TTTTAACTCT TACTAGTTGT CGTAGTTCGT CGACTCGAAC TTACACTCCT TCTGCAATAA

481 CCAGATTCAC CGATAACAGC CTTCTCATTT TCTGGCGTTA ACCGGCTACG AAGAAGGAG
    GGTCTAAGTG GCTATTGTCG GAAGAGTAAA AGACCGCAAT TGGCCGATGC TTCTTTCCTC

541 AACCCCCATG TCCGATACAT AGAACAAACA CATACTAAAT TGGAGCACTC TGTGTGTGCA
    TTGGGGGTAC AGGCTATGTA TCTTGTTTGT GTATGATTTA ACCTCGTGAG ACACACACGT

601 AATGAAATGA GAAAAGTTTC CAAGTCTTCA ACTCATCCAC AACATAATCC TAATGAAAAT
    TTACTTTACT CTTTTCAAAG GTTCAGAAGT TGAGTAGGTG TTGTATTAGG ATTACTTTTA

661 GAAATTCTAG TAGCTGACAC TTATGACCAA AGTCAATCTC CAATGGCCAA AGCACATGGA
    CTTTAAGATC ATCGACTGTG AATACTGGTT TCAGTTAGAG GTTACCGGTT TCGTGTACCT

721 ACAAGCAGCT ATACCCCTGA TAAGTCATCT TTTAATTTAG CTACAGTTGT TGCTGAAACA
    TGTTCGTCGA TATGGGACT ATTCAGTAGA AAATTAAATC GATGTCAACA ACGACTTTGT

781 CTTGGACTTG GTGTTCAAGA AGAATCTGAA ACTCAAGGTC CCATGAGCCC CCTTGGTGAT
    GAACCTGAAC CACAAGTTCT TCTTAGACTT TGAGTTCCAG GGTACTCGGG GGAACCACTA

841 GAGCTCTACC ACTGTCTGGA AGGAAATCAC AAGAAACAGC CTTTTGAGGA ATCTACAAGA
    CTCGAGATGG TGACAGACCT TCCTTTAGTG TTCTTTGTCG GAAAACTCCT TAGATGTTCT

901 AATACTGAAG ATAGTTTAAG ATTTTCAGAT TCTACTTCAA AGACTCCTCC TCAAGAAGAA
    TTATGACTTC TATCAAATTC TAAAAGTCTA AGATGAAGTT TCTGAGGAGG AGTTCTTCTT

951 TTACCTACTC GAGTGTCATC TCCTGTATTT GGAGCTACCT CTAGTATCAA AAGTGGTTTA
    AATGGATGAG CTCACAGTAG AGGACATAAA CCTCGATGGA GATCATAGTT TTCACCAAAT
```

Figure 2B-(1)

```
1021 GATTTGAATA CAAGTTTGTC CCCTTCTCTT TTACAGCCTG GGAAAAAAAA ACATCTGAAA
     CTAAACTTAT GTTCAAACAG GGGAAGAGAA AATGTCGGAC CCTTTTTTTT TGTAGACTTT

1081 ACACTCCCTT TTAGCAACAC TTGTATATCT AGATTAGAAA AAACTAGATC AAAATCTGAA
     TGTGAGGGAA AATCGTTGTG AACATATAGA TCTAATCTTT TTTGATCTAG TTTTAGACTT

1141 GATAGTGCCC TTTTCACACA TCACAGTCTT GGGTCTGAAG TGAACAAGAT CATTATCCAG
     CTATCACGGG AAAAGTGTGT AGTGTCAGAA CCCAGACTTC ACTTGTTCTA GTAATAGGTC

1201 TCATCTAATA AACAGATACT TATAAATAAA AATATAAGTG AATCCCTAGG TGAACAGAAT
     AGTAGATTAT TTGTCTATGA ATATTTATTT TTATATTCAC TTAGGGATCC ACTTGTCTTA

1261 AGGACTGAGT ACGGTAAAGA TTCTAACACT GATAAACATT TGGAGCCCCT GAAATCATTG
     TCCTGACTCA TGCCATTTCT AAGATTGTGA CTATTTGTAA ACCTCGGGGA CTTTAGTAAC

1321 GGAGGCCGAA CATCCAAAAG GAAGAAAACT GAGGAAGAAA GTGAACATGA AGTAAGCTGC
     CCTCCGGCTT GTAGGTTTTC CTTCTTTTGA CTCCTTCTTT CACTTGTACT TCATTCGACG

1381 CCCCAAGCTT CTTTTGATAA AGAAAATGCT TTCCCTTTTC CAATGGATAA TCAGTTTTCC
     GGGGTTCGAA GAAAACTATT TCTTTTACGA AAGGGAAAAG GTTACCTATT AGTCAAAAGG

1441 ATGAATGGAG ACTGTGTGAT GGATAAACCT CTGGATCTGT CTGATCGATT TTCAGCTATT
     TACTTACCTC TGACACACTA CCTATTTGGA GACCTAGACA GACTAGCTAA AAGTCGATAA

1501 CAGCGTCAAG AGAAAAGCCA AGGAAGTGAG ACTTCTAAAA ACAAATTTAG GCAAGTGACT
     GTCGCAGTTC TCTTTTCGGT TCCTTCACTC TGAAGATTTT TGTTTAAATC CGTTCACTGA

1561 CTTTATGAGG CTTTGAAGAC CATTCCAAAG GGCTTTTCCT CAAGCCGTAA GGCCTCAGAT
     GAAATACTCC GAAACTTCTG GTAAGGTTTC CCGAAAAGGA GTTCGGCATT CCGGAGTCTA

1621 GGCAACTGCA CGTTGCCCAA AGATTCCCCA GGGGAGCCCT GTTCACAGGA ATGCATCATC
     CCGTTGACGT GCAACGGGTT TCTAAGGGGT CCCCTCGGGA CAAGTGTCCT TACGTAGTAG

1681 CTTCAGCCCT TGAATAAATG CTCTCCAGAC AATAAACCAT CATTACAAAT AAAAGAAGAA
     GAAGTCGGGA ACTTATTTAC GAGAGGTCTG TTATTTGGTA GTAATGTTTA TTTTCTTCTT

1741 AATGCTGTCT TTAAAATTCC TCTACGTCCA CGTGAAAGTT TGGAGACTGA GAATGTTTTA
     TTACGACAGA AATTTTAAGG AGATGCAGGT GCACTTTCAA ACCTCTGACT CTTACAAAAT

1801 GATGACATAA AGAGTGCTGG TTCTCATGAG CCAATAAAAA TACAAACCAG GTCAGACCAT
     CTACTGTATT TCTCACGACC AAGAGTACTC GGTTATTTTT ATGTTTGGTC CAGTCTGGTA

1861 GGAGGATGTG AACTTGCATC AGTTCTTCAG TTAAATCCAT GTAGAACTGG TAAAATAAAG
     CCTCCTACAC TTGAACGTAG TCAAGAAGTC AATTTAGGTA CATCTTGACC ATTTTATTTC

1921 TCTCTACAAA ACAACCAAGA TGTATCCTTT GAAAATATCC AGTGGAGTAT AGATCCGGGA
     AGAGATGTTT TGTTGGTTCT ACATAGGAAA CTTTTATAGG TCACCTCATA TCTAGGCCCT

1981 GCAGACCTTT CTCAGTATAA AATGGATGTT ACTGTAATAG ATACAAAGGA TGGCAGTCAG
     CGTCTGGAAA GAGTCATATT TTACCTACAA TGACATTATC TATGTTTCCT ACCGTCAGTC

2041 TCAAAATTAG GAGGAGAGAC AGTGGACATG GACTGTACAT TGGTTAGTGA AACCGTTCTC
     AGTTTTAATC CTCCTCTCTG TCACCTGTAC CTGACATGTA ACCAATCACT TTGGCAAGAG
```

Figure 2B-(2)

```
2101 TTAAAAATGA AGAAGCAAGA GCAGAAGGGA GAAAAAAGTT CAAATGAAGA AAGAAAAATG
     AATTTTTACT TCTTCGTTCT CGTCTTCCCT CTTTTTTCAA GTTTACTTCT TTCTTTTTAC

2161 AATGATAGCT TGGAAGATAT GTTTGATCGG ACAACACATG AAGAGTATGA ATCCTGTTTG
     TTACTATCGA ACCTTCTATA CAAACTAGCC TGTTGTGTAC TTCTCATACT TAGGACAAAC

2221 GCAGACAGTT TCTCCCAAGC AGCAGATGAA GAGGAGGAAT TGTCTACTGC CACAAAGAAA
     CGTCTGTCAA AGAGGGTTCG TCGTCTACTT CTCCTCCTTA ACAGATGACG GTGTTTCTTT

2281 CTACACACTC ATGGTGATAA ACAAGACAAA GTCAAGCAGA AAGCGTTTGT GGAGCCGTAT
     GATGTGTGAG TACCACTATT TGTTCTGTTT CAGTTCGTCT TTCGCAAACA CCTCGGCATA

2341 TTTAAAGGTG ATGAAAGAGA GACTAGCTTG CAAAATTTTC CTCATATTGA GGTGGTTCGG
     AAATTTCCAC TACTTTCTCT CTGATCGAAC GTTTTAAAAG GAGTATAACT CCACCAAGCC

2401 AAAAAAGAGG AGAGAAGAAA ACTGCTTGGG CACACGTGTA AGGAATGTGA AATTTATTAT
     TTTTTTCTCC TCTCTTCTTT TGACGAACCC GTGTGCACAT TCCTTACACT TTAAATAATA

2461 GCAGATATGC CAGCAGAAGA AAGAGAAAAG AAATTGGCTT CCTGCTCAAG ACACCGATTC
     CGTCTATACG GTCGTCTTCT TTCTCTTTTC TTTAACCGAA GGACGAGTTC TGTGGCTAAG

2521 CGCTACATTC CACCCAACAC ACCAGAGAAT TTTTGGGAAG TTGGTTTTCC TTCCACTCAG
     GCGATGTAAG GTGGGTTGTG TGGTCTCTTA AAAACCCTTC AACCAAAAGG AAGGTGAGTC

2581 ACTTGTATGG AAAGAGGTTA TATTAAGGAA GATCTTGATC CTTGTCCTCG TCCAAAAAGA
     TGAACATACC TTTCTCCAAT ATAATTCCTT CTAGAACTAG GAACAGGAGC AGGTTTTTCT

2641 CGTCAGCCTT ACAACGCAAT ATTTTCTCCA AAAGGCAAGG AGCAGAAGAC ATAG
     GCAGTCGGAA TGTTGCGTTA TAAAAGAGGT TTTCCGTTCC TCGTCTTCTG TATC
```

Figure 2B-(3)

"MNILGSSCGSPNSADTSSDFKDLWTKLKECHDREVQGLQVKVTK
LKQERILDAQRLEEFFTKNQQLREQQKVLHETIKVLEDRLRAGLCDRCAVTEEHMRKK
QQEFENIRQQNLKLITELMNERNTLQEENKKLSEQLQQKIENDQQHQAAELECEEDVI
PDSPITAFSFSGVNRLRRKENPHVRYIEQTHTKLEHSVCANEMRKVSKSSTHPQHNPN
ENEILVADTYDQSQSPMAKAHGTSSYTPDKSSFNLATVVAETLGLGVQEESETQGPMS
PLGDELYHCLEGNHKKQPFEESTRNTEDSLRFSDSTSKTPPQEELPTRVSSPVFGATS
SIKSGLDLNTSLSPSLLQPGKKKHLKTLPFSNTCISRLEKTRSKSEDSALFTHHSLGS
EVNKIIQSSNKQILINKNISESLGEQNRTEYGKDSNTDKHLEPLKSLGGRTSKRKKT
EEESEHEVSCPQASFDKENAFPFPMDNQFSMNGDCVMDKPLDLSDRFSAIQRQEKSQG
SETSKNKFRQVTLYEALKTIPKGFSSSRKASDGNCTLPKDSPGEPCSQECIILQPLNK
CSPDNKPSLQIKEENAVFKIPLRPRESLETENVLDDIKSAGSHEPIKIQTRSDHGGCE
LASVLQLNPCRTGKIKSLQNNQDVSFENIQWSIDPGADLSQYKMDVTVIDTKDGSQSK
LGGETVDMDCTLVSETVLLKMKKQEQKGEKSSNEERKMNDSLEDMFDRTTHEEYESCL
ADSFSQAADEEEELSTATKKLHTHGDKQDKVKQKAFVEPYFKGDERETSLQNFPHIEV
VRKKEERRKLLGHTCKECEIYYADMPAEEREKKLASCSRHRFRYIPPNTPENFWEVGF
PSTQTCMERGYIKEDLDPCPRPKRRQPYNAIFSPKGKEQKT"

Figure 3

```
Ad2   243R  ²²²ciedllhepgq----PLDLSckrprp  243      SEQ ID NO:5

Ad12  235R  ²⁰⁹sildliqeeereqtvPVDLSvkrprcn 235      SEQ ID NO:6

Ad7   261R  ²³⁹kledlleggdg----PLDLStrklprq 261      SEQ ID NO:7

Ad4   257R  ²³⁵clddllqggde----PLDLCtrkrprh 257      SEQ ID NO:8

Ad40  249R  ²²⁵ciedll--eedptdePLNLSlkrpkcs 249      SEQ ID NO:9

SA7   231R  ²⁰⁷slhdli--eeveqtvPLDLSlkrsrsn 231      SEQ ID NO:10

Human CtIP ⁴⁷⁵mdnqfsmngdcvmdkPLDLSdrfsaiq  501      SEQ ID NO:11
```

Figure 5

CtIP —[PLDLS]—

CtIPΔ —[LASQC]—

GST    GST-CtIP    GST-CtIPΔ    1/10 Input

CtBPical regulatory activities (Linder et al., Onco-
CTIP, A NOVEL PROTEIN THAT INTERACTS WITH CTBP AND USES THEREFOR

REFERENCE TO RELATED APPLICATIONS

This application claims priority to, and incorporates herein by reference, U.S. Provisional Application Ser. No. 60/069,362 filed Dec. 12, 1997.

REFERENCE TO GOVERNMENT SUPPORT

This invention was made with U.S. Government support under Grant No. CA-33616 from the National Cancer Institute. The U.S. Government has certain rights in the invention.

BACKGROUND OF THE INVENTION (1) Field of the Invention

This invention generally relates to the field of cancer and, more particularly, to a method and compositions for diagnosing the malignancy of a tumor as well as to compositions and methods for suppressing tumor growth.

(2) Description of Related Art

The E1 a region of human adenovirus types 2 and 5 encodes two major proteins of 289 amino acids and 243 amino acids (289k and 243R) that differ only by an internal 46 amino acid region unique to the 289R protein. These E1A proteins immortalize primary animal cells and cooperate with other cellular and viral oncogenes in oncogenic transformation. These activities are dictated by the binding of several cellular proteins with the E1A proteins. For example, the N-terminal half of E1A proteins, which is encoded by exon 1 of the E1a gene, interacts with cellular growth-regulatory proteins such as the retinoblastoma gene product (pRb) and related proteins (p107 and p130), as well as p300, a CREB binding protein-related transcription factor implicated in transcriptional repression of certain genes (Moran, supra; Eckner et al., *Genes Dev.* 8:867–884, 1993; Arany et al., *Nature* 374:81–84, 1995; Lundblad et al., *Nature* 374:85–88, 1995). The interaction between E1A proteins and the cellular proteins pRb, p107 and p130 cause these cellular proteins to release the E2F transcription factor, thus activating gene expression. For review, see Dyson and Harlow, *Cancer Surveys* 12: 161–195, 1992; Nevins, J. R., *Science* 258: 424–429, 1992; Moran, E., *Curr. Op. Gen. Dev.* 3, 63–70, 1993; Mymryk, J. S., et al., *Int. J. Onc.* 4, 2131–2141, 1994. Interaction of E1A proteins with p300 releases C-CAF, a cellular acetyl transferase, from the p300/C-CAF complex resulting in activation of transcription by chromatin remodeling (Yang et al., *Nature* 382:319–324, 1996). Thus, the transforming activities encoded by exon 1 of the adenovirus E1a region appear to be linked to interactions with cellular proteins and the resulting regulation of transcription.

Although the functions of exon 2-encoded domains of E1A proteins have been studied less intensively, these domains have been implicated in certain positive and negative transcriptional regulatory activities (Linder et al., *Oncogene* 7:439–443, 1992; Bondesson et al., *EMBO J.* 11:3347–3354, 1992; Mymryk, J. S. et al., *J. Virol.* 67 6922–2928, 1993). Exon 2 is required for immortalization (Subramanian, T., et al., *Oncogene* 4:415–520, 1989; Quinlan, M. P. et al., *J. Virol.* 66:2020–2040, 1992) and induction of Ad2/5-specific cytotoxic lymphocytes (Urbanelli et al., *Virol.* 173:607–614, 1989). In addition, exon 2 influences the extent of oncogenic transformation. Deletions within the C-terminal 67 amino acids of the E1A 243R protein enhance E1A/T24 ras cooperative transformation (Subramanian, supra; Douglas, J. L., et al., *Oncogene* 6:2093–2103, 1991), and tumorigenesis of transformed cells in syngeneic and athymic rodent models (Subramanian, supra). Importantly, exon 2 also plays a role in tumor metastasis. Expression of wt E1A efficiently suppresses the metastatic potential of tumor cells (Pozzatti, R. et al., *Science* 232:223–227, 1986; Pozzatti, R., et al., *Mol. Cell. Biol.* 8:2984–2988, 1988, Steeg et al., *Cancer Res.* 48:6550–6554, 1988). In contrast, cells expressing E1A proteins lacking the C-terminal 67 amino acids are highly metastatic (Linder et al., supra; Subramanian, supra). Thus, the E1A protein region encoded by exon 2 appears to negatively modulate in vitro transformation, tumorigenesis and metastasis. These activities have been localized within a 14 amino acid region (residues 225 to 238) near the C-terminus of the 243R protein (Boyd, J. M., et al., *EMBO J.* 12:469–478, 1993). These transformation restraining activities of the C-terminal region of E1A correlate with the interaction of a 48 kD cellular phosphoprotein termed CtBP (E1A C-terminal Binding Protein) (Boyd et al., supra). CtBP binds to E1A proteins via a 5 amino acid motif, PLDLS, which corresponds to residues 233–237 of the 243R protein. E1A mutants having amino acid substitutions within this motif do not form complexes with CtBP (Schaeper, U., et al., *Proc. Natl. Acad. Sci.* 92:10667–10671, 1995) and do not have oncogenesis-restraining activities (Schaeper et al., *J. Biol. Chem.* 273:8549–8552, 1998).

Although interaction of adenovirus E1A proteins with the cellular protein CtBP appears to lead to suppression of tumorigenesis and tumor metastasis of cells transformed with E1A and activated T24 Ras oncogene over expression of CtBP by itself does not appear to exert a significant effect on tumorigenesis and tumor metastasis. One explanation for the inability to detect the effect of CtBP activity could be the fact that expression levels of endogenous CtBP are relatively high. CtBP was found to be abundantly expressed in a variety of human and mouse tissues as well as tissue culture cell lines (Boyd et al., supra). If CtBP functions in a complex with other cellular proteins, overexpression of recombinant CtBP may not cause an effect if cellular cofactors are rate limiting. Thus, to understand the role of CtBP in modulating oncogenesis it would be useful to identify and characterize cellular proteins that interact with CtBP.

SUMMARY OF THE INVENTION

Briefly, therefore, the present invention is directed to the identification and isolation of substantially purified proteins that bind to the cellular protein CtBP. Accordingly, the inventor herein has succeeded in discovering a novel human CtBP-binding protein, which is designated CtIP for CtBP-Interacting Protein. The inventor herein has also discovered that CtIP contains the same five amino acid motif (PLDLS) found in adenovirus E1A proteins to which CtBP binds and that deletion of this binding motif in CtIP abolishes its binding to CtBP.

The invention thus provides isolated and purified CtIP polypeptides. A preferred CtIP polypeptide identified herein comprises the human CtIP amino acid sequence shown in FIG. 3 (SEQ ID NO:2).

The present invention also provides isolated polynucleotides encoding a CtIP polypeptide. Preferred polynucleotides identified herein encode the amino acid sequence shown in FIG. 3. A particularly preferred polynucleotide comprises SEQ ID NO:3.

A recombinant cell comprising a polynucleotide encoding for expression a CtIP polypeptide is also within the scope of this invention. The recombinant cell can be used in a method for producing CtIP.

In another embodiment, the invention provides isolated polynucleotides comprising a human nucleotide sequence complementary to a nucleotide sequence encoding a CtIP polypeptide or CtIP fragment. A preferred complementary sequence is SEQ ID NO:4 (FIG. 2B, bottom strand). The invention also provides isolated polynucleotides that specifically hybridize to polynucleotides consisting of SEQ ID NO:1, SEQ ID NO:3 or SEQ ID NO:4. These complementary and hybridizing polynucleotides can be used in methods for detecting the CtIP gene and transcription products thereof, as well as in isolating CtIP-encoding polynucleotides from other mammalian and nonmammalian species.

In yet another embodiment, the present invention provides a composition comprising a CtIP polypeptide or fragment and a carrier that facilitates delivery of the CtIP polypeptide or fragment into a target cell.

The present invention also provides polyclonal and monoclonal antibodies that specifically react with CtIP or CtIP fragments and methods for purifying CtIP or detecting its expression using such antibodies.

A method for determining malignancy of a cell in a patient is also provided. The method comprises detecting CtIP expression in the cell, wherein an amount of CtIP expression that is lower than the amount in normal cell indicates the cell is malignant. In one embodiment, the method comprises detecting a CtIP polypeptide with an antibody that specifically reacts with CtIP or a fragment thereof. In other embodiments, the method comprises detecting CtIP mRNA with a polynucleotide probe or by amplifying a target sequence in CtIP mRNA.

In another embodiment, the invention provides a method for inhibiting neoplasia of target cells in a patient which comprises treating the patient with an effective amount of a CtIP polypeptide or fragment. The patient may be treated by administering the CtIP polypeptide or biologically active fragment to the patient or by administering to the patient a polynucleotide encoding the CtIP polypeptide or fragment, through which CtIP or fragment is expressed in the target cells.

The invention also provides a method for identifying agents that inhibit neoplasia of cells which involves determining whether a candidate agent disrupts binding of CtIP and CtBP.

Among the several advantages found to be achieved by the present invention, therefore, may be noted the provision of a new protein, CtIP, which is useful in a method for inhibiting neoplasia of cells; the provision of polynucleotides encoding CtIP; the provision of methods for obtaining CtIP by recombinant techniques; the provision of methods for determining the malignancy of a target cell in a patient; the provision of methods for identifying agents that inhibit neoplasia, and the provision of methods that can detect alterations in the CtIP gene.

BRIEF DESCRIPTION OF THE DRAWINGS

FIG. 2A illustrates the nucleotide sequence of a CtIP cDNA (SEQ ID NO:1).

FIGS. 2B-1, 2B-2, and 2B-3 illustrate the nucleotide sequence encoding CtIP and its complementary sequence (SEQ ID NOs:3 and 4, respectively).

FIG. 3 illustrates the predicted amino acid sequence of CtIP.

FIG. 5 illustrates a sequence alignment of CtIP with E1A proteins from different adenoviruses, with the boxed residues designating the PLDLS sequence motif that is conserved among E1A proteins and essential for CtBP interaction.

DETAILED DESCRIPTION OF THE PREFERRED EMBODIMENTS

Figure 1:
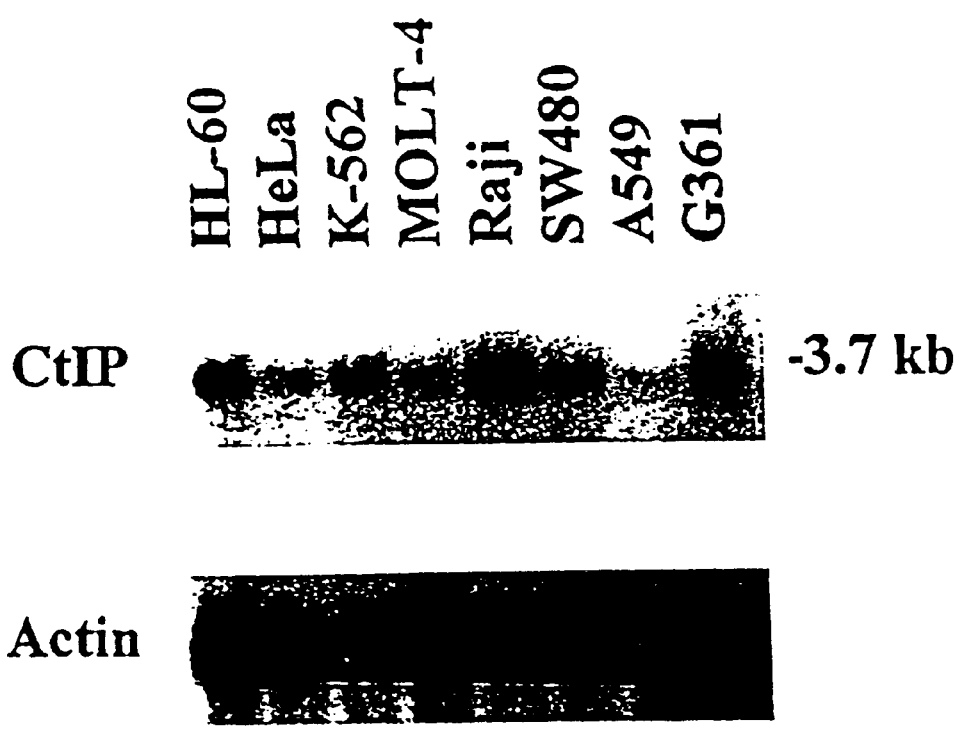
FIG. 1 illustrates expression of CtIP in human cancer cell lines showing a northern blot of RNA prepared from human cancer cell lines (Clontech) analyzed using [$^{32}$P]-labeled probes derived from the cDNA clone pGAD#15 or Actin cDNA.

The present invention is based upon the identification, isolation and sequencing of cDNA clones that encode a novel human protein that binds the cellular protein CtBP, which the inventor has named CtIP. As described in more detail below, CtIP was discovered by yeast-two hybrid screening of a cDNA library for GAL4 fusion proteins that bind to CtBP which identified a partial cDNA encoding a human cellular protein that binds to CtBP. The 5' end of the CtIP cDNA sequence was obtained by rapid amplification of the 5' ends of the human mRNA. The composite cDNA sequence consists of 3247 bp (FIG. 2) and contains a nucleotide sequence (FIG. 2A) which encodes the CtIP protein of 897 amino acids (FIG. 3).

As shown in the examples below, CtIP binds with CtBP and this binding is disrupted by adenovirus E1A proteins binding to CtBP. As the CtBP-binding region of E1A has been implicated in transcriptional regulatory activity encoded by exon 1 (Sollerbrant, et al., *Nucl. Acids. Res.*, 24:2578–2584, 1996), it is believed that CtIP has a transcriptional regulatory activity that plays a role in the observed oncogenesis-restraining activity of the C-terminal region of E1A proteins. A data bank search based on sequence properties (PROPSEARCH, Hobohm et al., *J. Mol. Biol* 251:390–399, 1995) has revealed that CtIP shares similarities with certain mammalian proteins involved in DNA repair. Thus, it is believed that CtIP may suppress neoplasia or oncogenesis through DNA repair and/or transcriptional regulatory activities.

In one embodiment, the invention provides CtIP polypeptides and fragments thereof. As used herein, the term "CtIP" means both CtIP polypeptides and CtIP fragments. Reference to a CtIP polypeptide herein is intended to be construed to include polypeptides of any origin which are substantially homologous to and which are biologically equivalent to the human CtIP characterized and described herein. Such substantially homologous polypeptides may be native to any tissue or species and, similarly, biological activity can be characterized in any of a number of biological assay systems.

The term "biologically equivalent" is intended to mean that a CtIP polypeptide of the present invention is capable of demonstrating some or all of the tumor suppressing or CtBP-binding properties in a similar fashion, although not necessarily to the same degree, as the recombinantly produced human CtIP identified herein. By "substantially homologous" it is meant that the degree of sequence identity between human CtIP and a CtIP ortholog from another mammalian species is at least about 75% sequence identity and between human and non-mammalian orthologs is at least about 65% identity.

Sequence identity or percent identity is intended to mean the percentage of same residues between two sequences aligned using the Clustal method (Higgins et al, *Cabios* 8:189–191, 1992) of multiple sequence alignment in the Lasergene biocomputing software (DNASTAR, INC, Madison, Wis.). In this method, multiple alignments are carried out in a progressive manner, in which larger and larger alignment groups are assembled using similarity scores calculated from a series of pairwise alignments. Optimal sequence alignments are obtained by finding the maximum alignment score, which is the average of all scores between the separate residues in the alignment, determined from a residue weight table representing the probability of a given amino acid change occurring in two related proteins over a given evolutionary interval. Penalties for opening and lengthening gaps in the alignment contribute to the score. The default parameters used with this program are as follows: gap penalty for multiple alignment=10; gap length penalty for multiple alignment=10; k-tuple value in pairwise alignment=1; gap penalty in pairwise alignment=3; window value in pairwise alignment=5; diagonals saved in pairwise alignment=5. The residue weight table used for the alignment program is PAM250 (Dayhoff et al., in *Atlas of Protein Sequence and Structure*, Dayhoff, Ed., NBRF, Washington, Vol. 5, suppl. 3, p. 345, 1978).

To determine percent sequence identity between two sequences, the number of identical amino acids in the aligned sequences is divided by the total number of amino acids in the reference sequence. As used herein, the reference sequence is human CtIP when determining its percent identity with an ortholog from another species or with an engineered CtIP polypeptide. Percent conservation is calculated by adding the number of identical residues to the number of positions at which the two residues represent a conservative substitution (defined as having a log odds value of greater than or equal to 0.3 in the PAM250 residue weight table) and dividing by the total number of amino acids in the reference sequence. Preferred conservative amino acid changes are: R-K; E-D, Y-F, L-M; V-I, Q-H.

Also included within the meaning of substantially homologous is any CtIP polypeptide isolated by virtue of cross-reactivity with antibodies specific to human CtIP or whose encoding nucleotide sequences, including genomic DNA, mRNA or cDNA, may be isolated through hybridization with the complementary sequences shown in FIG. 2B or fragments thereof. It will also be appreciated by one skilled in the art that naturally occurring allelic variants of the human CtIP sequence disclosed herein may exist and such allelic variants are also intended to be included in the present invention.

Conservatively substituted CtIP proteins retaining the biological activity of naturally occurring CtIP are also within the scope of the present invention. Conservative amino acid substitutions refer to the interchangeability of residues having similar side chains. Conservatively substituted amino acids can be grouped according to the chemical properties of their side chains. For example, one grouping of amino acids includes those amino acids have neutral and hydrophobic side chains (A, V, L, I, P, W, F, and M); another grouping is those amino acids having neutral and polar side chains (G, S, T, Y, C, N, and Q); another grouping is those amino acids having basic side chains (K, R, and H); another grouping is those amino acids having acidic side chains (D and E); another grouping is those amino acids having aliphatic side chains (G, A, V, L, and I); another grouping is those amino acids having aliphatic-hydroxyl side chains (S and T); another grouping is those amino acids having amine-containing side chains (N, Q, K, R, and H); another grouping is those amino acids having aromatic side chains (F, Y, and W); and another grouping is those amino acids having sulfur-containing side chains (C and M). Preferred conservative amino acid substitutions groups are: R-K; E-D, Y-F, L-M; V-I, and Q-H.

As used herein, a CtIP polypeptide can also include modifications of the human CtIP amino acid sequence identified herein, including sequences in which one or more amino acids have been inserted, deleted or replaced with a different amino acid or a modified or unusual amino acid, as well as modifications such as glycosylation or phosphorylation of one or more amino acids so long as the polypeptide containing the modified sequence retains the biological activity of CtIP. Inserted or deleted amino acid(s) can be added to or removed from the N-terminus, C-terminus or within the naturally-occurring amino acid sequence. By retaining the biological activity, it is meant that the modified polypeptide can suppress neoplasia when expressed in a cell although not necessarily to the same degree as that of naturally occurring human CtIP. As used herein "neoplasia" means the conversion of normal cells into benign or malignant tumor cells and thus includes tumorigenesis, oncogenesis and related terms, and is also intended to include metastasis.

Fragments of CtIP are also encompassed by the present invention. Such fragments may be of any length but preferably retain the biological activity of CtIP or are antigenic. The minimum length of such biologically active or antigenic fragments can readily be determined by those skilled in the art using known techniques. Antigenic fragments are capable of eliciting CtIP-specific antibodies when administered to a host animal and includes those smaller fragments that require conjugation to a carrier molecule to be immunogenic. Typically, antigenic fragments will be at least 5 or 6 amino acids in length and may be any length up to the length of human CtIP. Preferably, an antigenic fragment comprises 10 to 12 amino acids of SEQ ID NO:2 and more preferably, an antigenic fragment will comprise at least 15 to 20 amino acids, or more, or SEQ ID NO:2.

It is also believed that particular discrete fragments of CtIP comprising the CtBP-binding motif PLDLS, or analogues thereof, can serve to inhibit CtBP from binding to CtIP, thereby making more unbound CtIP available to suppress neoplasia of cells. Such CtBP-binding inhibitor fragments are also included within the scope of the invention. One preferred binding inhibitor fragment is shown in FIG. 5 and consists of SEQ ID NO:11. Another preferred fragment consists of the pentapeptide PLDLS (SEQ ID NO:12).

The present invention also includes non-peptidal substances such as peptide mimetics which possess the binding-inhibiting activity of CtIP fragments. The techniques for development of peptide mimetics are well known in the art. (See for example, Navia and Peattie, *Trends Pharm Sci* 14:189–195, 1993; Olson et al, *J Med Chem* 36:3039–3049 which are incorporated by reference). Typically this involves identification and characterization of the interaction between a protein target and its peptide ligand using X-ray crystallography and nuclear magnetic resonance technology. For example, it is believed that at least one target protein for CtIP peptides is CtBP. Using information on a normal peptide-protein complex along with computerized molecular modeling, a pharmacophore hypothesis is developed and analogue compounds are made and tested in an assay system.

A preferred CtIP polypeptide according to the present invention is prepared by recombinant DNA technology although it is believed that CtIP can be isolated in purified form from human cells. By "pure form" or "purified form" or "substantially purified form" it is meant that a CtIP composition is substantially free of other proteins which are not CtIP. Preferably, a substantially purified CtIP composition comprises at least about 50 percent CtIP on a molar basis compared to total proteins or other macromolecular species present. More preferably, a substantially purified CtIP composition will comprise at least about 80 to about 90 mole percent of the total protein or other macromolecular species present and still more preferably, at least about 95 mole percent or greater.

Recombinant CtIP may be made by expressing the DNA sequences encoding CtIP in a suitable transformed host cell. Using methods well known in the art, the DNA encoding CtIP may be linked to an expression vector, transfected into a host cell and conditions established that are suitable for expression of CtIP by the transfected cell.

Any suitable expression vector may be employed to produce recombinant CtIP such as, for example, the mammalian expression vector pCB6 (Brewer, *Meth Cell Biol* 43:233–245, 1994) or the *E. coli* pET expression vectors, specifically, pET-30a (Studier et al., *Methods Enzymol* 185:60–89, 1990). Other suitable expression vectors for expression in mammalian and bacterial cells are known in the art as are expression vectors for use in yeast or insect cells. Baculovirus expression systems can also be employed.

A number of cell types may be suitable as host cells for expression of recombinant CtIP. Mammalian host cells include, but are not limited to, monkey COS cells, Chinese Hamster Ovary (CHO) cells, human kidney 293 cells, human epidermal A431 cells, human Colo 205 cells, 3T3 cells, CV-1 cells, other transformed primate cell lines, normal diploid cells, cell strains derived from in vitro culture of primary tissue, primary explants, HeLa cells, mouse L cells, BHK, HL-60, U937, HaK and Jurkat cells. Yeast strains that may act as suitable host cells include *Saccharomyces cerevisiae, Schizosaccharomyces pombe*, Kluyveromyces strains, Candida, and any other yeast strain capable of expressing heterologous proteins. Host bacterial strains include *Escherichia coli, Bacillus subtilis, Salmonella typhimurium* and any other bacterial strain capable of expressing heterologous proteins. If the polypeptide is made in yeast or bacteria, it may be necessary to modify the polypeptide, for example, by phosphorylation or glycosylation of the appropriate sites using known chemical or enzymatic methods, to obtain a biologically active polypeptide.

A polypeptide according to the invention may also be expressed in transgenic animals, e.g., cows, goats, pigs, or sheep whose somatic or germ cells contain a nucleotide sequence encoding human CtIP or variant thereof.

The expressed CtIP polypeptide can be purified using known purification procedures, such as gel filtration and ion exchange chromatography. Purification may also include affinity chromatography using an agent that will specifically bind the CtIP polypeptide, such as a polyclonal or monoclonal antibody raised against CtIP or fragment thereof. Other affinity resins typically used in protein purification may also be used such as concanavalin A-agarose, heparin-toyopearl® or Cibacrom blue 3GA Sepharose®. Purification of CtIP can also include one or more steps involving hydrophobic interaction chromatography using such resins as phenyl ether, butyl ether, or propyl ether.

It is also contemplated that a CtIP polypeptide may be expressed as a fusion protein to facilitate purification. Such fusion proteins, for example, include a CtIP amino acid sequence fused to a histidine tag such as when expressed in the pET bacterial expression system as well as the CtIP amino acid sequence fused to the amino acid sequence of maltose binding protein (MBP), glutathione-S-transferase (GST) or thioredoxin (TRX). Similarly, the polypeptide of the invention can be tagged with a heterologous epitope and subsequently purified by immunoaffinity chromatography using an antibody that specifically binds such epitope. Kits for expression and purification of such fusion proteins and tagged proteins are commercially available.

CtIP and fragments thereof may also be produced by chemical synthesis using methods known to those skilled in the art.

The present invention also encompasses isolated polynucleotides comprising nucleotide sequences that encode any of the CtIP polypeptides described herein. As used herein, a polynucleotide includes DNA and/or RNA and thus the nucleotide sequences recited in the Sequence Listing as DNA sequences also include the identical RNA sequences with uracil substituted for thymine residues. Preferred nucleotide sequences included in the invention are those encoding the human CtIP amino acid sequence shown in FIG. 3. Particularly preferred polynucleotides comprise SEQ ID NO:3. It is understood by the skilled artisan that degenerate nucleotide sequences can encode the CtIP amino acid sequences described herein and these are also intended to be included within the present invention. Such degenerate nucleotide sequences include modifications of naturally-occurring sequences in which at least one codon is substituted with a corresponding redundant codon preferred by a given host cell, such as *E. coli* or insect cells, so as to improve expression of recombinant CtIP therein. Polynucleotides within the scope of this invention do not include isolated chromosomes.

The present invention also encompasses vectors comprising an expression regulatory element operably linked to any of the CtIP-encoding nucleotide sequences included within the scope of the invention. This invention also includes host cells, of any variety, that have been transformed with such vectors.

In yet another embodiment, a polynucleotide which specifically hybridizes to a human CtIP-encoding polynucleotide or to its complement is provided. Specific hybridization is defined herein as the formation of hybrids between a polynucleotide, including oligonucleotides, and a specific reference polynucleotide (e.g., a polynucleotide comprising a nucleotide sequence encoding human CtIP ) wherein the polynucleotide preferentially hybridizes to the specific reference polynucleotide over other non CtIP polynucleotides. Specifically hybridizing oligonucleotides are typically at least 15 nucleotides in length and are preferably at least 17 to at least 20 nucleotides long. Other preferred lengths include at least 22 to at least 25 nucleotides. Specific hybridization is preferably done under high stringency conditions which, as well understood by those skilled in the art, can readily be determined by adjusting several factors during hybridization and during the washing procedure, including temperature, ionic strength, length of hybridization or washing times, and concentration of formamide (see for example, Sambrook et al., 1989, supra).

The present invention also includes nucleic acid sequences which encode for CtIP polypeptides that have CtBP binding activity and that preferentially bind anti-human CtIP antibodies over other antibodies that do not bind to human CtIP.

Methods are also provided herein for producing recombinant CtIP polypeptides. The method involves culturing a cell which contains an expression vector comprising a nucleotide sequence encoding a CtIP polypeptide and isolating the expressed CtIP polypeptide.

The present invention also includes therapeutic or pharmaceutical compositions comprising a CtIP polypeptide in an effective amount for suppressing neoplasia of target cells in a patient and a method comprising administering a therapeutically effective amount of the CtIP polypeptide to a cell ex vivo or in vivo. The compositions and methods are useful for treating a variety of diseases including but not limited to hyperplasia, neoplasia, lymphoproliferative diseases, autoimmune disorders, transplant rejection, and the like.

In certain circumstances, it may be desirable to modulate or decrease the amount of CtIP expressed. Thus, in another aspect of the present invention, CtIP anti-sense oligonucleotides can be made and a method utilized for diminishing the level of expression of CtIP, respectively, by a cell comprising administering one or more CtIP anti-sense oligonucleotides. By CtIP anti-sense oligonucleotides reference is made to oligonucleotides that have a nucleotide sequence that interacts through base pairing with a specific complementary nucleic acid sequence involved in the expression of CtIP such that the expression of CtIP is reduced. Preferably, the specific nucleic acid sequence involved in the expression of CtIP is a genomic DNA molecule or mRNA molecule that contains sequences of the CtIP gene. Thus, the invention contemplates CtIP anti-sense oligonucleotides that can base pair to flanking regions of the CtIP gene, untranslated regions of CtIP mRNA or the coding sequence for CtIP. The term complementary to a nucleotide sequence in the context of CtIP antisense oligonucleotides and methods therefor means sufficiently complementary to such a sequence as to allow hybridization to that sequence in a cell, i.e., under physiological conditions. The CtIP antisense-oligonucleotides preferably comprise a sequence containing from about 8 to about 100 nucleotides and more preferably the CtIP antisense oligonucleotides comprise from about 15 to about 30 nucleotides. The CtIP antisense oligonucleotides can also contain a variety of modifications that confer resistance to nucleolytic degradation such as, for example, modified internucleoside linkages (Uhlmann and Peyman, *Chemical Reviews* 90:543–548, 1990; Schneider and Banner, *Tetrahedron Lett* 31:335, 1990), modified nucleic acid bases and/or sugars and the like.

The therapeutic or pharmaceutical compositions of the present invention can be administered by any suitable route known in the art including for example intravenous, subcutaneous, intramuscular, transdermal, intrathecal or intracerebral. Administration can be either rapid as by injection or over a period of time as by slow infusion or administration of slow release formulation. For treating tissues in the central nervous system, administration can be by injection or infusion into the cerebrospinal fluid (CSF). When it is intended that CtIP be administered to cells in the central nervous system, administration can be with one or more agents capable of promoting penetration of CtIP across the blood-brain barrier.

CtIP can also be linked or conjugated with agents that provide desirable pharmaceutical or pharmacodynamic properties. For example, CtIP can be coupled to any substance known in the art to promote penetration or transport across the blood-brain barrier such as an antibody to the transferrin receptor, and administered by intravenous injection. (See for example, Friden et al., *Science* 259:373–377, 1993). Furthermore, CtIP can be stably linked to a polymer such as polyethylene glycol to obtain desirable properties of solubility, stability, half-life and other pharmaceutically advantageous properties. (See for example Davis et al. *Enzyme Eng* 4:169–73, 1978; Burnham, *Am J Hosp Pharm* 51:210–218, 1994).

Preferably, CtIP is administered with a carrier such as liposomes or polymers containing a targeting moiety to facilitate delivery of CtIP to targeted cells. Examples of targeting moieties include but are not limited to antibodies, ligands or receptors to specific cell surface molecules. The CtIP polypeptide or fragment can also be modified to include a specific transit peptide that facilitates delivering CtIP into the cytoplasm of cells. Examples of such transit peptides include but are not limited to the TAT protein from HIV-1 (Frankel et al., *Cell* 55:1189–1193, 1988; Fawell et al., *Proc. Natl. Acad. Sci. USA* 91:664–668, 1994; Ezhevsky *Proc. Natl. Acad. Sci. USA* 94:10699–10704, 1997), the third helix of the Antennapedia homeodomain (Derossi et al., *J. Biol. Chem.* 271:18188–18193, 1996), and penetratins, which are 16 mer peptides derived from the Antennapedia homeodomain (Derossi et al., *Trends Cell Biol.* 8:84–87, 1998). Alternatively, CtIP can be delivered directly into target cells by microinjection.

For nonparenteral administration, the compositions can also include absorption enhancers which increase the pore size of the mucosal membrane. Such absorption enhancers include sodium deoxycholate, sodium glycocholate, dimethyl-$\beta$-cyclodextrin, lauroyl-1-lysophosphatidylcholine and other substances having structural similarities to the phospholipid domains of the mucosal membrane.

The compositions are usually employed in the form of pharmaceutical preparations. Such preparations are made in a manner well known in the pharmaceutical art. One preferred preparation utilizes a vehicle of physiological saline solution, but it is contemplated that other pharmaceutically acceptable carriers such as physiological concentrations of other non-toxic salts, five percent aqueous glucose solution, sterile water or the like may also be used. It may also be desirable that a suitable buffer be present in the composition. Such solutions can, if desired, be lyophilized and stored in a sterile ampoule ready for reconstitution by the addition of sterile water for ready injection. The primary solvent can be aqueous or alternatively non-aqueous. CtIP can also be incorporated into a solid or semi-solid biologically compatible matrix which can be implanted into tissues requiring treatment.

The carrier can also contain other pharmaceutically-acceptable excipients for modifying or maintaining the pH, osmolarity, viscosity, clarity, color, sterility, stability, rate of dissolution, or odor of the formulation. Similarly, the carrier may contain still other pharmaceutically-acceptable excipients for modifying or maintaining release or absorption or penetration across the blood-brain barrier. Such excipients are those substances usually and customarily employed to formulate dosages for parenteral administration in either unit dosage or multi-dose form or for direct infusion into the cerebrospinal fluid by continuous or periodic infusion.

Dose administration can be repeated depending upon the pharmacokinetic parameters of the dosage formulation and the route of administration used.

It is also contemplated that certain formulations containing CtIP are to be administered orally. Such formulations are preferably encapsulated and formulated with suitable carriers in solid dosage forms. Some examples of suitable carriers, excipients, and diluents include lactose, dextrose, sucrose, sorbitol, mannitol, starches, gum acacia, calcium phosphate, alginates, calcium silicate, microcrystalline cellulose, polyvinylpyrrolidone, cellulose, gelatin, syrup, methyl cellulose, methyl- and propylhydroxybenzoates, talc, magnesium, stearate, water, mineral oil, and the like. The formulations can additionally include lubricating agents, wetting agents, emulsifying and suspending agents, preserving agents, sweetening agents or flavoring agents. The compositions may be formulated so as to provide rapid, sustained, or delayed release of the active ingredients after administration to the patient by employing procedures well known in the art. The formulations can also contain substances that diminish proteolytic degradation and promote absorption such as, for example, surface active agents.

The specific dose is calculated according to the approximate body weight or body surface area of the patient or the volume of body space to be occupied. The dose will also be calculated dependent upon the particular route of administration selected. Further refinement of the calculations necessary to determine the appropriate dosage for treatment is routinely made by those of ordinary skill in the art. Exact dosages are determined in conjunction with standard dose-response studies. It will be understood that the amount of the composition actually administered will be determined by a practitioner, in the light of the relevant circumstances including the condition or conditions to be treated, the choice of composition to be administered, the age, weight, and response of the individual patient, the severity of the patient's symptoms, and the chosen route of administration.

The invention also provides a method for determining malignancy of at least one cell in a patient which comprises detecting CtIP expression in the cell. Typically, the method involves detecting CtIP expression in a sample obtained from a patient tissue known or suspected to be cancerous. The term "determining malignancy" as used herein in the context of a patient with neoplastic disease is intended to include the estimation of prognosis in terms of probable outcome of the disease and prospect for recovery, the monitoring of the disease status or the recurrence of the disease, or the determining of a preferred therapeutic regimen for the patient. For example, as discussed above, it is believed that Adenovirus E1A proteins compete with CtIP for interaction with CtBP and the resulting increase in the amount of CtIP that is free of CtBP plays a role in the oncogenesis-restraining activity of E1A proteins. Thus, the amount of CtIP that is unbound to CtBP in a cancer cell relative to the amount in normal cells would be expected to be indicate whether a cell is malignant and/or the degree of malignancy. For example, a cancer which contains no detectable or only low amounts of CtIP as compared to normal cells would be expected to be more malignant and thus the prognosis poorer than for cancers in which the amount of CtIP detected is closer to or equal to the amount present in normal cells. Thus the term "detecting CtIP expression" as used herein in the context of determining malignancy of cells means detecting and/or quantifying CtIP and/or mRNA encoding CtIP, although quantifying does not require actual measurement of amounts of the protein or mRNA and may include qualitative comparisons.

In one embodiment of the method, CtIP expression in a cell is detected by contacting proteins from the cell with an antibody which specifically reacts with CtIP or a CtIP fragment and detecting binding of the antibody to CtIP. Any method known in the art for detecting specific proteins can be used. Such methods include, but are not limited to, immunodiffusion, immunoelectrophoresis, immunochemical methods, binder-ligand assays, immunohistochemical techniques, agglutination and complement assays. (for example see Basic and Clinical Inmmunology, Sites and Terr, eds., Appleton & Lange, Norwalk, Conn. pp 217–262, 1991).

Preferred methods for detecting CtIP are binder-ligand immunoassay methods using an antibody to human CtIP or fragment thereof. Numerous competitive and non-competitive protein binding immunoassays are well known in the art. Antibodies employed in such assays may be unlabeled, for example as used in agglutination tests, or labeled for use in a wide variety of assay methods. Labels that can be used include radionuclides, enzymes, fluorescers, chemiluminescers, enzyme substrates or co-factors, enzyme inhibitors, particles, dyes and the like for use in radioimmunoassay (RIA), enzyme immunoassays, e.g., enzyme-linked immunosorbent assay (ELISA), fluorescent immunoassays and the like.

Polyclonal or monoclonal antibodies to CtIP or to an epitope thereof can be made for use in immunoassays by any of a number of methods known in the art. By epitope reference is made to an antigenic determinant of a polypeptide. An epitope could comprise 3 amino acids in a spatial conformation which is unique to the epitope. Methods of determining the spatial conformation of amino acids are known in the art, and include, for example, x-ray crystallography and 2 dimensional nuclear magnetic resonance. Generally an epitope comprises at least 6 contiguous amino acids of a polypeptide.

In another embodiment, malignancy of a cell is determined by detecting CtIP mRNA in the cell. CtIP mRNA may be detected by hybridizing a polynucleotide probe to mRNA of the cell or to cDNA prepared from this mRNA. High stringency conditions can be used in order to prevent false positives, that is hybridization to non-CtIP nucleotide sequences. When using sequences that are not perfectly complementary to a CtIP-encoding polynucleotide or a fragment thereof, less stringent conditions could be used, however, this would be a less preferred approach because of the likelihood of false positives. The stringency of hybridization is determined by a number of factors during hybridization and during the washing procedure, including temperature, ionic strength, length of time and concentration of formamide. These factors are outlined in, for example, Sambrook et al. (Sambrook, et al., 1989, supra).

In order to increase the sensitivity of detection of CtIP mRNA in a cell, a target CtIP sequence in cDNA prepared from mRNA of the cell can be amplified using any technique known in the art. Such techniques include reverse transcription/polymerization chain reaction (RT/PCR), ligase chain reaction methods, including gap LCR (G-LCR) and other variations, or self-sustained sequence replication (3SR) and its various modifications. In addition, the CtIP mRNA can be detected directly by asymmetric gap LCR (AG-LCR). See, e.g., Leckie et al., "Infectious Disease Testing by Ligase Chain Reaction" in *Molecular Biology and Biotechnology*, R. A. Myers, ed., pp. 463–466, VCH Publishers, 1995.

In some instances it is desirable to determine whether the CtIP gene is intact in the patient's genome or in a particular tissue within the patient. For example, a number of cancers are caused by or are made more malignant by the inactivation of a tumor suppressor gene such as p53, NF1, MCC, and the retinoblastoma (RB) gene. By an intact CtIP gene it is meant that there are no alterations in the gene such as point mutations, deletions, insertions, chromosomal breakage, chromosomal rearrangements and the like wherein such alteration might alter production of CtIP or alter its biological activity, stability or the like to cause cancer or make the patient more susceptible to neoplastic diseases. Conversely, by a non-intact CtIP gene it is meant that such alterations are present.

Thus, in one embodiment of the present invention a method is provided for detecting and characterizing any alterations in the CtIP gene. The method comprises providing a polynucleotide that specifically hybridizes to a CtIP cDNA, genomic DNA or a fragment thereof. Typically, patient genomic DNA is isolated from a cell sample from the patient and digested with one or more restriction endonucleases such as, for example, TaqI and AluI. Using the Southern blot protocol, which is well known in the art, this assay determines whether a patient or a particular tissue in a patient has an intact CtIP gene or an abnormality in the CtIP gene. Hybridization to the CtIP gene would involve denaturing the chromosomal DNA to obtain a single-stranded DNA; contacting the single-stranded DNA with a gene probe associated with the CtIP gene sequence; and identifying the hybridized DNA-probe to detect chromosomal DNA containing at least a portion of the human CtIP gene.

The term "probe" as used herein refers to a structure comprised of a polynucleotide which forms a hybrid structure with a target sequence, due to complementarity of probe sequence with a sequence in the target region. The probes need not contain the exact complement of the target sequence, but must be sufficiently complementary to selectively hybridize with the strand being detected. By selective hybridization or specific hybridization it is meant that a polynucleotide preferentially hybridizes to a target polynucleotide. Oligomers suitable for use as probes may contain a minimum of about 8–12 contiguous nucleotides which are complementary to the targeted sequence and preferably a minimum of about 15 or 17 nucleotides although polynucleotide probes of about 20 to 25 nucleotides and up to about 100 nucleotides or even greater are within the scope of this invention.

The CtIP gene probes of the present invention can be DNA or RNA oligonucleotides and can be made by any method known in the art such as, for example, excision, transcription or chemical synthesis. Probes may be labeled with any detectable label known in the art such as, for example, radioactive or fluorescent labels or enzymatic marker. Labeling of the probe can be accomplished by any method known in the art such as by PCR, random priming, end labeling, nick translation or the like. One skilled in the art will also recognize that other methods not employing a labeled probe can be used to determine the hybridization. Examples of methods that can be used for detecting hybridization include Southern blotting, fluorescence in situ hybridization, and single-strand conformation polymorphism with PCR amplification.

Hybridization is typically carried out at 25–45° C., more preferably at 32–40° C. and more preferably at 37–38° C. The time required for hybridization is from about 0.25 to about 96 hours, more preferably from about one to about 72 hours, and most preferably from about 4 to about 24 hours.

CtIP gene abnormalities can also be detected by using the PCR method or any other known DNA amplification method which uses oligonucleotides to identify a target sequence within a longer sequence to be amplified. The term "oligonucleotide" as used herein refers to a short strand of DNA or RNA typically ranging in length from about 8 to about 30 bases and are preferably bout 15 nucleotides to about 25 nucleotides. The primers are selected to be substantially complementary to the strand of DNA being amplified. Therefore, the primers need not reflect the exact sequence of the template, but must be sufficiently complementary to selectively hybridize or specifically hybridize with the strand being amplified. By selective hybridization or specific hybridization it is meant that a polynucleotide preferentially hybridizes to a target polynucleotide. After amplification, the amplification product may be sequenced and the sequence analyzed by comparison with the CtIP nucleotide sequences disclosed herein to identify alterations which might change activity or expression levels or the like.

The invention also provides methods for inhibiting neoplasia of target cells in a patient comprising treating the patient with CtIP. In one embodiment, the treating step comprises administering to the patient a polynucleotide comprising a nucleotide sequence encoding CtIP operably linked to a promoter that produces expression of CtIP in the target cells. The polynucleotide can comprise an expression plasmid, a retrovirus vector, an adenovirus vector, an adenovirus associated vector (AAV) or other vector used in the art to deliver genes into cells. Alternatively, the polynucleotide can be administered to the cell by microinjection. It is also contemplated that CtIP-encoding polynucleotide can be administered by coinfection with a replication-defective adenovirus expressing CtIP and another replication competent adenovirus that complements the replication defective virus to increase the expression of CtIP in the infected cells.

Preferably, the polynucleotide is selectively delivered to target cells within the patient so as not to affect other tissues. Targeted delivery of the polynucleotide can be done for example by using delivery vehicles such as polycations, liposomes or viral vectors containing targeting moieties that recognizes and binds a specific marker on the target cell. Such methods are known in the art, see, e.g., U.S. Pat. No. 5,635,383. Another targeted delivery approach uses viral vectors that can only replicate in specific cell types which is accomplished by placing the viral genes necessary for replication under the transcriptional control of a response element for a transcription factor that is only active in the target cell. See, e.g., U.S. Pat. No. 5,698,443.

In another embodiment, the patient is treated with CtIP by administering a CtIP polypeptide or CtIP fragment to the patient. Preferably, the CtIP polypeptide or CtIP fragment is administered with a carrier that facilitates its delivery into the cell, such as liposomes. The liposomes may have targeting moieties exposed on the surface such as antibodies, ligands or receptors to specific cell surface molecules to limit delivery of CtIP to targeted cells. Liposome drug delivery is known in the art (see, e.g., Amselem et al., *Chem. Phys. Lipid* 64:219–237, 1993). Alternatively, one or more of the polypeptides of the complex can be modified to include a specific transit peptide that is capable of delivering CtIP into the cytoplasm of a cell or CtIP can be delivered directly into a cell by microinjection.

Also included within the invention is a method for identifying agents that inhibit neoplasia of cells. The method comprises determining whether a candidate agent disrupts binding of CtIP and CtBP. Any binding assay known in the art may be used. Typically, binding assays involve one of two formats: an immobilized CtIP polypeptide can be used to bind labeled CtBP, or conversely, immobilized CtBP can be used to bind labeled CtIP polypeptides. In each case, the labeled polypeptide is contacted with the immobilized polypeptide under conditions that permit specific binding of the polypeptide to form a CtIP:CtBP complex in the absence of the candidate agent. Particular conditions may be selected by the skilled artisan according to conventional methods. The method can be used for high-throughput screening of agent banks such as compound libraries, peptide libraries and the like. Alternatively, the binding assay is performed in vivo in a cell, such as a yeast two-hybrid system in which a reporter gene is expressed when a complex between CtIP and CtBP is formed. Such assays are described in U.S. Pat. No. 5,834,209. An agent that inhibits binding would reduce the amount of reporter gene expression as compared to the amount of reporter gene expression in the absence of the agent.

Preferred embodiments of the invention are described in the following examples. Other embodiments within the scope of the claims herein will be apparent to one skilled in the art from consideration of the specification or practice of the invention as disclosed herein. It is intended that the specification, together with the examples, be considered exemplary only, with the scope and spirit of the invention being indicated by the claims which follow the examples.

Brief Description of the Materials and Methods Used in the Examples

Yeast Two Hybrid Screening.

Screenings were carried out using the yeast stain Y153 (MATa, gal4, gal80, leu2, ura3, trp1, his3, ade2, URA3::GAL1-lacZ, Lys2::GAL-HIS3) (Durfee et al., *Genes Dev.* 7:555–569, 1993). Yeast cells were grown in YPD medium (1% yeast extract, 2% bactopeptone, 2% sucrose), or selective minimal medium, SD medium lacking specified amino acids (2% sucrose, 0.67% nitrogen base plus amino acid dropout solution; Rose et al., 1990).

Yeast two hybrid screens were carried out as described previously (Durfee et al., supra; Chien et al., *Proc. Natl. Acad. Sci. USA* 88:9578–9582, 1991). A plasmid (pGb-CtBP) expressing a fusion protein consisting of the DNA binding domain of GAL4 (amino acids 1–147) and the entire CtBP protein was used as the bait. A GAL4 activation domain tagged HeLa cell cDNA library (Clontech) was used as the prey. The yeast cells (strain Y153) were cotransformed with the bait plasmid and the cDNA library (prey) by the Li/Ac method (Rose et al., 1990). The transformants were selected for growth in SD medium that lacked histidine and leucine and also supplemented with 25 mM 3AT. After incubation at 30° C. for 3 to 5 days, yeast colonies were transferred onto nitrocellulose filters and screened for β-galactosidase activity by X-gal blue/white filter lift assay (Breeden and Nasmyth, 1985). Positive colonies were subcultured in selective media and plasmid DNA was recovered (Hoffmann and Winston, 1987). cDNA plasmids were identified by their ability to complement the leuB mutation of *E. coli* HB101 (Chien et al., 1991). HB101 cells transformed by electroporation were grown on M9 plates supplemented with 40 µg/ml proline, 1 mM thiamine and 100 µg/ml ampicillin. cDNA plasmids recovered by this method were retested individually by yeast two hybrid studies for interaction with CtBP and various heterologous protein baits (Boyd et al., 1994; Kamine et al., 1996). cDNA clones that interacted only with the CtBP bait were chosen for further studies.

5' RACE Reactions

5' sequences of CtIP cDNA were isolated by rapid amplification of cDNA ends (RACE) reaction using a commercially available kit (Gibco/BRL). First strand cDNA synthesis was carried out with the CtIP specific primer AS2 using poly(A) RNA from Raji cells (provided by Eric Uhlmann) as template. PCR reactions were performed with CtIP specific primers Cip-RACE1 or Cip-RACE-2 and anchor primers provided by the manufacturer (Gibco/BRL). PCR conditions were modified to optimize results: 35 cycles, 1 min at 94° C., 30 s at 63° C., 2 min at 72° C. For sequence analysis, the final PCR products were cloned into Bluescript KS+ (Stratagene) between SpeI and EcoR1 (taking advantage of the internal EcoRI site present in the cDNA of CtIP).

DNA Sequence Analysis

Both strands of various cDNA clones were sequenced by dideoxy chain termination method using Sequenase version 2.0 (United States Biochemical Corporation) or the fmol sequencing system (Promega).

Northern Blot Analysis

Human multiple tissue northern (MTN) blots or human cancer cell line MTN blots (Clontech), containing approximately 2 µg of poly(A) RNA per lane, were probed with $^{32}$P-labeled cDNA probes (CtBP, CtIP, or human Actin) under high stringency conditions. Mouse (MTN) blots were probed under low stringency conditions following the instructions of the manufacturer (Clontech). $^{32}$P-dCTP labeled probes were prepared using a random primer extension labeling kit (DuPont/NEN). cDNA fragments isolated from pGAD#9 (BamH1/BglII fragment) served as template for labeling reactions.

Expression and Purification of GST-fusion Proteins

Fresh overnight cultures of *E. coli* B121 cells (Promega) transformed pGEX-5X3 or pGST-CtBP or pGST-CtIP or GST-Cter (Boyd et al., supra) or GST-Cter (dl1135). Transformed cells were diluted 1/10 in LB medium plus 0.2 mM IPTG and 100 µg/ml ampicillin and grown at 25° C. for 12–16 hours. Bacterial cultures were collected by centrifugation at 4° C. and the pellets were resuspended in 1/100 of original volume NETN buffer (50 mM Tris, pH 8.0, 100 mM NaCl, 1 mM EDTA, 0.5% NP40) containing 0.5% milk. Bacterial cultures expressing GST-CtBP (GST-30) were resuspended in 1/20 of culture volume and stored at −70 C. prior to purification (to reduce proteolysis of GST-CtBP). Cells expressing GST-CtIP were resuspended in 1/20 volume NETN plus 1% Triton X100. All cells were lysed by sonication (2X 1 min pulses) and precleared by centrifugation at high speed (15 min at 10000 rpm). Glutathione agarose beads (Sigma) were prewashed in NETN buffer and incubated with bacterial lysate for 15 min at 4° C. Beads were then washed 3X with NETN buffer and stored at 4° C. An aliquot of the beads was resuspended in 2X SDS sample buffer (0.125 M Tris/HCl, pH 6.8, 4% SDS, 20% glycerol, 2% β-mercaptoethanol, 10 µ/ml Bromophenol Blue), boiled for two min, and the supernatant analyzed by SDS-PAGE. Gels were stained with coomassie blue solution (0.1% coomassie brilliant blue, 40% methanol) to estimate protein concentrations. 1 ml of protein-conjugated beads was prepared from 500 ml to 2000 ml of bacterial culture depending on protein expression and recovery. Protein concentrations ranged from 20 mg/ml beads for GST to approximately 0.2 mg/ml beads for GST-CtIP. For binding experiments, protein concentrations of GST-beads were normalized by mixing with glutathione agarose beads.

Preparation of Polyclonal Antisera

Polyclonal antisera were raised against GST-CtIP as described by Harlow and Lane (1988). Affinity purified GST-fusion proteins were eluted by boiling in 2 X SDS-electrophoresis sample buffer and separated on SDS-polyacrylamide (8%) gels. Gels were rinsed in $H_2O$ and stained with coomassie blue (0.2% in $H_2O$). Protein bands were excised and mixed with Freund's adjuvant prior to injection. New Zealand rabbits were injected subcutaneously with 50 to 100 μg protein every three to four weeks. Serum was collected 10–14 days after injection and stored at −20° C. The IgG fraction was purified from GST-CtBP antiserum by protein A column chromatography (Pierce).

In vitro Protein Binding and Affinity Chromatography

Proteins expressed by in vitro transcription/translation (using TNT transcription/translation expression system, Promega) were labeled by incorporation of [$^{35}$S]-methionine. The translation mixtures (50 μl) were clarified and diluted in 1 ml of respective binding buffer (E1A lysis buffer: 250 mM NaCl, 0.1% NP40, 50 mM Hepes, pH 7.0; buffer A: 150 mM NaCl, 0.1% NaCl, 0.1% NP40, 50 mM Tris, pH 7.5 containing protease inhibitors aprotinin (20 μ/ml) and leupeptin (200 μg/ml) and preincubated with GST beads for 1 to 2 hours at 4° C. on rotor. For binding experiments using labeled cell extracts, lysates were preincubated with GST and glutathione agarose beads for 12 to 16 hours. The precleared lysates were divided equally among the immobilized GST or GST-fusion proteins (5 μg protein, 15 μl beads per binding reaction). After incubation at 4° C. for 1 to 2 hours, beads were washed six times with binding buffer, resuspended in 2X electrophoresis sample buffer and boiled for 2 min. Beads were pelleted and the supernatant was analyzed by SDS-Polyacrylamide gel electrophoresis. Gels were soaked in 1 M sodium salicylate as a fluorographic enhancer, dried and analyzed by autoradiography.

Competition Binding Experiments

Soluble E1A peptides representing the C-terminal 67 amino acids of E1A 243R or dl1135 were prepared from immobilized GST-Cter and GST-dl1135 by cleavage with factor $X_a$ (New England Biolabs). Beads containing 1 mg of protein (200 to 400 μl) were resuspended in 400 μl factor $X_a$ buffer (20 mM Tris pH 8.0, 100 mM NaCl, 2 mM $CaCl_2$) containing 8 units of factor $X_a$ (New England Biolabs) and incubated for 6 to 12 hours at room temperature. Beads and supernatants were analyzed for cleavage products by SDS-PAGE and visualized by coomassie blue staining to estimate peptide concentrations. The supernatant (containing cleaved E1A peptides) was mixed with in vitro labeled CtBP and added to GST-Cter and GST-CtIP immobilized on glutathione beads. Binding experiments were then carried out as described above.

Coimmunoprecipitation

For in vivo coimmunoprecipitation analyses, recombinant proteins (CtIP and CtBP) were coexpressed in BSC40 cells using the vaccinia virus/T7 RNA polymerase system (Ausubel, et al., *Current Protocols in Molecular Biology*, John Wiley & Sons, New York, 1992). BSC40 cells (5X $10^6$ cells/T75 $cm^2$ flask) were infected with recombinant vaccinia virus vTF7-3 (which expresses T7 RNA polymerase; Fuerst et al., *Proc. Natl. Acad. Sci. USA* 83:8122–8126, 1986) in serum free medium (DMEM) at 10 PFU per cell and then transfected with 10 μg of appropriate expression plasmids using LipofectAMINE (Gibco/BRL). Five hours later cell culture medium was supplemented with 10% fetal calf serum. At 18 to 20 hours post infection, cells were labeled with $^{35}$S-methionine/cysteine mixture (500 μCi/T75 $cm^2$ flask). After labeling, all procedures were carried out on ice or at 4° C. Cells were rinsed twice with PBS and lysed by addition of E1A lysis buffer (1 ml/T75 $cm^2$ flask) supplemented with protease inhibitors aprotinin (20 μg/ml) and leupeptin (200 μg/ml). Cells were incubated for 30 min in lysis buffer to solubilized proteins. Lysates were clarified by centrifugation in an eppendorf centrifuge at high speed for 15 min and preincubated with protein A sepharose beads (Sigma) for at least one hour. The precleared lysate was then divided and mixed with respective monoclonal antibodies (MAb) or polyclonal antiserum and incubated for at least one hour. Protein A sepharose beads (Sigma) were then added and the incubation continued for one to two hours. Beads were pelleted and washed at least seven times with E1A lysis buffer. Samples were analyzed by gel electrophoresis and fluorography as described previously (Boyd et al., supra).

EXAMPLE 1

This example illustrates isolation of the cDNA clone.

The cDNA clones that code for proteins which bind with CtBP were cloned by two hybrid screening in yeast. The yeast reporter strain Y153 (Durfee et al., supra) was transformed with the bait plasmid (pGB-CtBP), expressing the entire coding sequence of CtBP fused in frame with the Gal4 DNA binding domain together with a Gal4-activation domain tagged HeLa cell cDNA library (Clontech). To identify putative CtBP interacting cDNA clones the yeast transformants were grown in selective media and screened for activation of the LacZ reporter gene by X gal filter lift assays. Six cDNA clones were isolated by this method. They were further tested for interaction with heterologous baits in yeast. Three clones, pGad#8, -#9 and #15 interacted specifically with CtBP, but not with the vector pGBT9 or three heterologous baits including E1A exon 2 (data not shown), suggesting that the proteins encoded by these cDNA clones interact specifically with CtBP. Sequence analysis revealed that clone #8 encoded the C-terminus of a known protein, the 70 kD subunit of KU (Reeves and Sthoeger, 1989), while pGAD#9 and pGAD#15 represent partial cDNA clones of a novel protein, the CtBP interacting protein, CtIP (CtBP-Interacting Protein).

EXAMPLE 2

This examples illustrates the isolation of full length cDNA of CtIP.

The cDNAs of the two other CtBP interacting cDNA clones, pGAD#9 and pGAD#15, were identical except for 153 base pair 5' coding sequences unique to clone #9, suggesting that they represent partial cDNA clones of the same protein, referred to as CtBP Interacting protein, CtIP. This was confirmed by northern blot analysis using multiple tissue blots (Clonetech). A $^{32}$P-labeled probe specific for the cDNA of clone #15 hybridized to a single mRNA species present in preparations from several tumor cell lines (FIG. 1). However, the transcript size of 3.7 kb was about 800 bp larger than the cDNA represented by clone #9. The predicted reading frame of clone #9 and clone #15, established in relation to the coding sequence of the GAL4 DNA binding domain contained several stop codons 3' to the coding region, suggesting that both cDNA clones encoded the carboxy-terminus of CtIP. To isolate additional 5' coding sequences of CtIP, 5' RACE reactions were performed using a commercially available kit (Clontech, Inc.) according to the manufacturer's protocol. 5' cDNA sequences were isolated that encoded an additional 31 amino acids in frame with the cDNA of clone #9 with a putative ATG start codon at position 300. The complete cDNA sequence is presented in FIG. 2A. The reading frame upstream of this ATG contains several stop codons, indicating that the ATG initiates the open reading frame. Thus, this sequence contains the complete 5' coding sequence of CtIP. The coding sequence of CtIP (FIG. 2B) codes for a protein of 897 aminoacids (FIG. 3), while clone #9 and clone #15 encode the C-terminal 864 and 835 residues of CtIP respectively.

EXAMPLE 3

This example illustrates in vitro binding of CtBP and CtIP.

Figure 4:
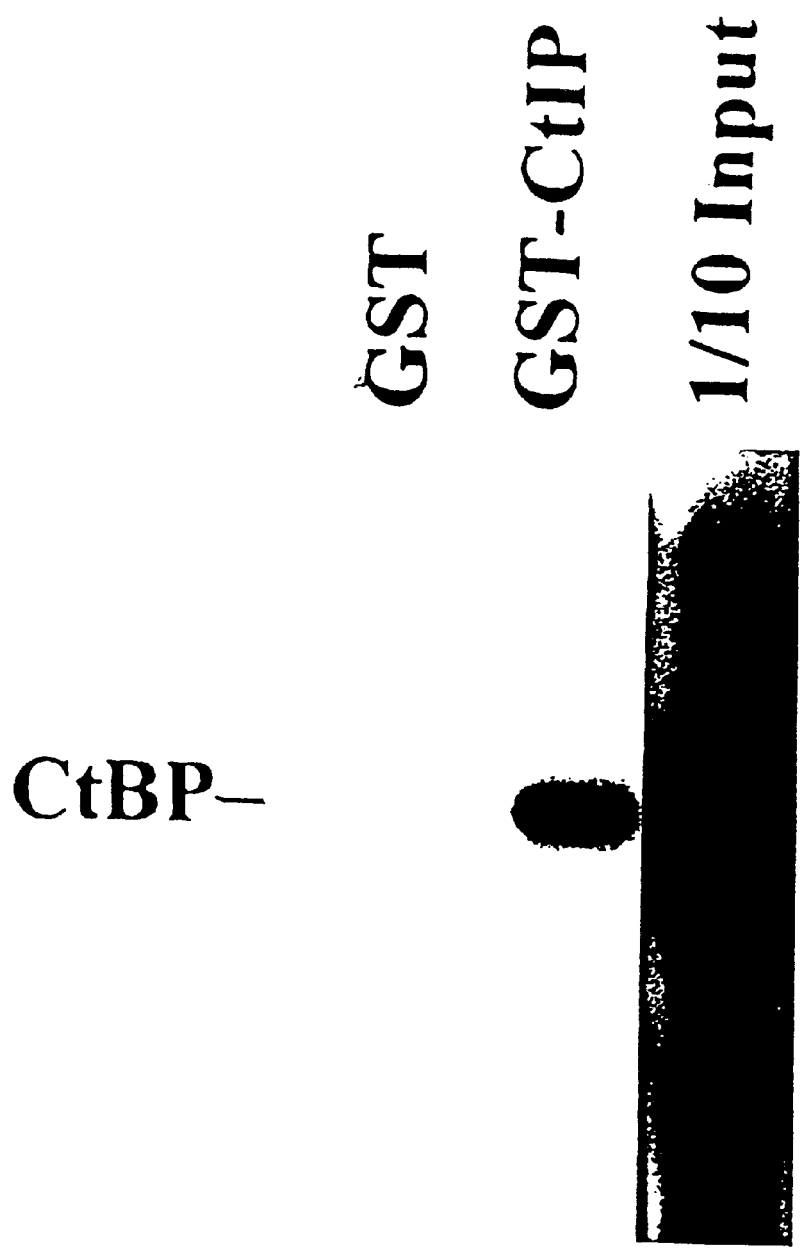
FIG. 4 illustrates that CtBP binds to immobilized GST-CtIP protein.

To confirm that CtIP could directly bind with CtBP, in vitro binding experiments were carried out. The cDNA of pGAD-#15 encoding residues 70 to 897 of CtIP was cloned into the expression vector pGEX-5X3 (Pharmacia) in frame with the GST gene. Bacterially expressed and affinity purified GST-CtIP as well as GST control were immobilized on glutathione agarose beads and tested for interaction with in vitro translated $^{35}$S-labeled CtBP. Bound proteins were eluted in SDS sample buffer and analyzed by SDS-PAGE and fluorography (FIG. 4). CtBP interacted specifically with GST-CtIP but not with GST, confirming that it could directly associate with CtIP in vitro.

EXAMPLE 4

This example illustrates the effect of PLDLS mutation on CtIP interaction with CtBP.

Figures 6A, 6B:
FIG. 6 illustrates the effect of a PLDLS mutation on CtBP interaction, showing in FIG. 6A the substitution of residues 490 to 494 of CtIP (PLDLS) with non conserved residues (LASQC) in a CtIP mutant (CtIPΔ) and in FIG. 6B an autoradiograph of binding products detected in an in vitro binding assay and analyzed by SDS/polyacrylamide gel (10%) electrophoresis.

Comparison of CtIP coding sequences with DNA sequences in the data base using BLAST analysis (Altschul et al., 1990) did not reveal significant sequence homologies to known proteins. However, upon close examination it was discovered that CtIP shares a five amino acid motif, PLDLS, with E1A (FIG. 5). These five residues are well conserved among E1A proteins of various adenovirus serotypes. By mutational analysis of Ad2 E1A, it had been previously shown that this region is required for efficient interaction with CtBP. To determine if these five residues are also essential for interaction of CtIP with CtBP, a CtIP mutant, CtIPΔ, was constructed in which PLDLS was substituted to LASQC (FIG. 6A). CtIP was expressed as GST-fusion protein and tested for interaction with in vitro translated CtBP (FIG. 6B). Binding of CtBP to CtIPΔ was significantly reduced compared to the interaction with wild type GST-CtIP, suggesting that the PLDLS sequence constitutes the CtBP binding motif of CtIP as well as E1A.

EXAMPLE 5

This example illustrates the in vivo interaction of CtIP and CtBP.

Figure 7:
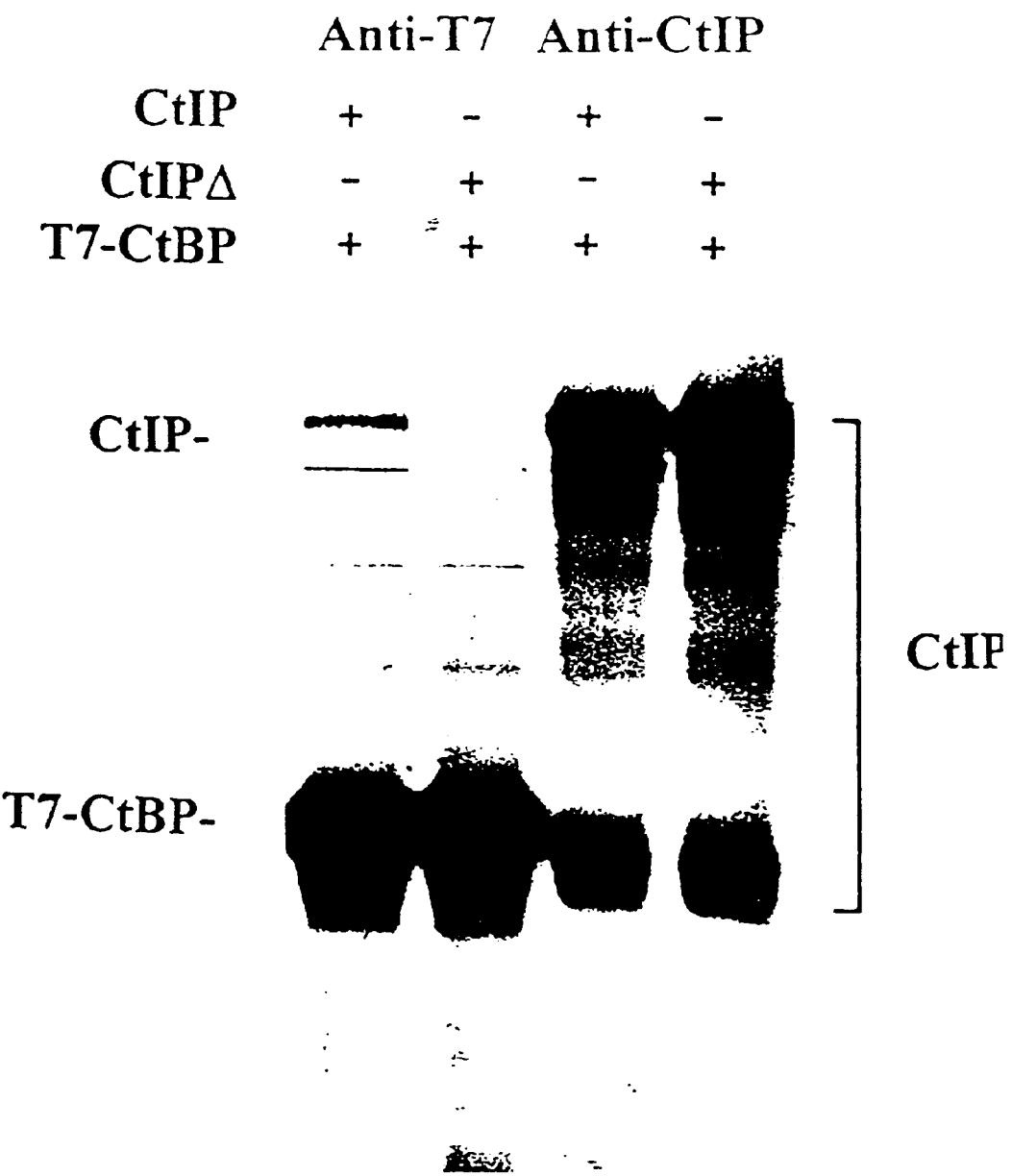
FIG. 7 illustrates coimmunoprecipitation of CtBP and CtIP from BSC40 cells co-expressing T7-epitope tagged CtBP and CtIP or CtIPΔ in BSC40 cells showing an autoradiograph of proteins precipitated with T7 mAb (Novagen) or CtIP antiserum (anti-CtIP) and analyzed by SDS/polyacrylamide gel (8%) electrophoresis.
Figure 8:
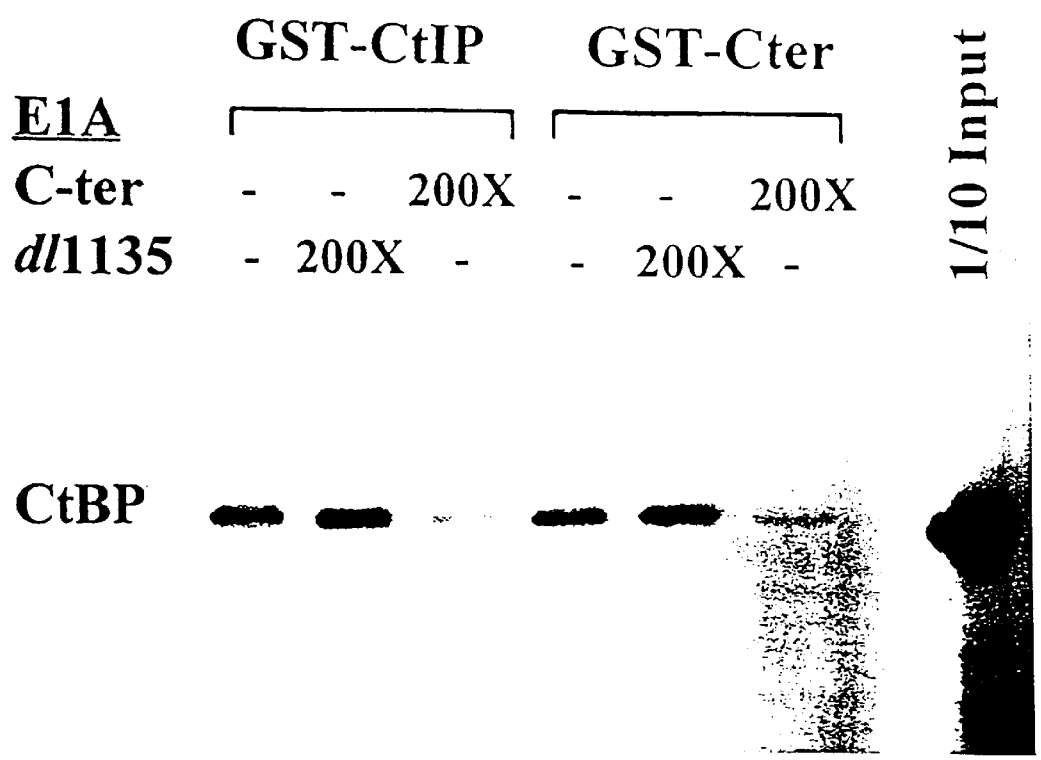
FIG. 8 illustrates that E1A and CtIP compete for CtBP interaction showing an autoradiograph of bound proteins analyzed by SDS/polyacrylamide gel (10%) electrophoresis.

To verify that CtIP could interact with CtBP in vivo a coimmunoprecipitation analysis was carried out. A T7 epitope tagged CtBP and full length CtIP (CtIP wt or mutant CtIPΔ) were coexpressed in BSC40 cells using the recombinant vaccinia virus/T7 expression system. After metabolic labeling with $^{35}$S-methionine/cysteine, cells were lysed in E1A lysis buffer (Harlow et al., 1986). The precleared lysate was divided and subjected to immunoprecipitation with either T7 mAb (Novagen) or CtIP antiserum (raised against GST-CtIP). As seen in FIG. 8 the majority of CtIP protein migrated with an apparent molecular weight of 125 kD on SDS gels, which is slightly larger than the predicted molecular weight of 100 kD. In addition, smaller CtIP products were also detected. Most likely they represent degradation products of the 125 kD CtIP protein. Importantly, CtIP but not CtIPΔ, which lacks the CtBP binding motif, coprecipitated with CtBP. CtBP migrated with a molecular weight (48 kD) close to that of some of the smaller CtIP products, but could be detected coprecipitating with CtBP antibody, but not with CtIP antibody (marked as dot in FIG. 7). These data confirm that CtBP interacts with full length CtIP and that this interaction can occur in vivo.

EXAMPLE 6

This example illustrates that E1A competes with CtIP for CtBP interaction.

Since CtIP contains the same CtBP binding motif as E1A, an experiment was performed to determine if E1A would compete with CtIP for CtBP interaction. It had been shown in earlier experiments that the GST-E1A fusion protein, GST-Cter, containing only the C-terminal 67 amino acids of E1A is capable of binding CtBP (Boyd et al., supra). Soluble E1A peptides were generated by proteolytic cleavage of immobilized GST-Cter fusion protein and utilized in competition binding experiments. CtBP was expressed by in vitro transcription/translation and then analyzed for binding to immobilized GST-CtIP or GST-Cter in the presence or absence of E1A peptide competitors. As demonstrated in FIG. 9, CtBP interacts well with GST-CtIP or the E1A fusion protein, GST-Cter. However, these interactions were significantly reduced in the presence of 200 fold molar concentration of wt E1A peptide (Cter), but not E1A dl135 which lacks the C6BP binding region. This result demonstrates that CtIP and E1A, which carry identical CtBP binding motifs, can compete for CtBP interaction.

EXAMPLE 7

This example illustrates the construction of AD-CtIP, an adenovirus vector for expressing CtIP.

The starting vector for the virus construction is pAd5LendCMV. This plasmid contains the Xho I C fragment (nucleotide number 1 to 5788 of adenovirus 5 (Ad5) with a deletion of the E1A gene and most of the E1B coding regions [Sac II (354) to Bgl II (3328)]. As a result of this deletion, this construct will not make any E1 polypeptides. The deleted region is substituted with the CMV immediate early (IE) promoter and a multiple cloning site containing Hind III, Kpn I and BamH I sites (other sites are not available because their multiple occurrence in the vector). The transcript from the CMV promoter will use the E1B polyadenylation site. Normally this vector is used for making recombinant adenoviruses that express proteins under the control of CMV promoter. For making AD-CtIP, an Apa I blunt-Kpn I fragment of pcDNA3-CtIP (CtIP cDNA) is cloned into BamH I blunt-Hind III digested pAd5Lend CMV and 5 µg of the resultant plasmid is transfected into human 293 cells (60 mm dish) along with 5 µg of pBHGE3 (Bett et.al., 1994) by the calcium phosphate method. The transfected cells are overlaid with growth medium containing 0.8% noble agar after 5 hours of transfection. After 7 days, the visible plaques are picked up, and screened for the expression of CtIP by western blot using rabbit polyclonal antibody raised against CtIP. After confirming, the correct virus (AD-CtIP) is amplified and titrated in 293 cells by plaque assay method. (Bett, A. J., Haddara, W., Prevec, L. and Graham, F. L. (1994). An efficient and flexible system for construction of adenovirus vectors with insertions or deletions in early regions 1 and 3, *Proc. Natl. Acad. Sci. USA* 91:8802–8806).

In view of the above, it will be seen that the several advantages of the invention are achieved and other advantageous results attained.

As various changes could be made in the above methods and compositions without departing from the scope of the invention, it is intended that all matter contained in the above description and shown in the accompanying drawings shall be interpreted as illustrative and not in a limiting sense.

All references cited in this specification, including patents and patent applications, are hereby incorporated by reference. The discussion of references herein is intended merely to summarize the assertions made by their authors and no admission is made that any reference constitutes prior art. Applicants reserve the right to challenge the accuracy and pertinency of the cited references.

What is claimed is:

1. An isolated and purified CtBP Interacting Protein (CtIP) polypeptide comprising SEQ ID NO:2.

2. A composition comprising the isolated and purified CtIP polypeptide of claim 1 and a carrier that facilitates delivery of the CtIP polypeptide into a target cell.

* * * * *

SEQUENCE LISTING

<160> NUMBER OF SEQ ID NOS: 12

<210> SEQ ID NO 1
<211> LENGTH: 3247
<212> TYPE: DNA
<213> ORGANISM: Homo sapiens

<400> SEQUENCE: 1

```
cgggtccggc cgctccgagc ccggccgcag cccccggctt aaagcgcggg ctgtccggag      60
ggtcggcttt cccaccgagg atttggcact ctggtgaggg ttttgggcga aagagaaaag     120
cgagcagccg tccttcacag cctcagaaag tgctcgcttc ccttcggggc tttcgcgaat     180
cccgaggcaa tctcggaggc ggtatttgac ctgtccaaag acgacttgat acctctataa     240
tgtaacagaa aaggtcagaa aatattaagc aagtagaagt gtggagcata ttaagcaaga     300
tgaacatctt gggaagcagc tgtggaagcc ctaactctgc agatacatct agtgacttta     360
aggacctttg gacaaaacta aaagaatgtc atgatagaga agtacaaggt ttacaagtaa     420
aagtaaccaa gctaaaacag gaacgaatct tagatgcaca aagactagaa gaattcttca     480
ccaaaaatca acagctgagg gaacagcaga aagtccttca tgaaaccatt aaagttttag     540
aagatcggtt aagagcaggc ttatgtgatc gctgtgcagt aactgaagaa catatgcgga     600
aaaaacagca agagtttgaa aatatccggc agcagaatct taaacttatt acagaactta     660
tgaatgaaag gaatactcta caggaagaaa ataaaaagct ttctgaacaa ctccagcaga     720
aaattgagaa tgatcaacag catcaagcag ctgagcttga atgtgaggaa gacgttattc     780
cagattcacc gataacagcc ttctcatttt ctggcgttaa ccggctacga agaaaggaga     840
acccccatgt ccgatacata gaacaaacac atactaaatt ggagcactct gtgtgtgcaa     900
atgaaatgag aaaagtttcc aagtcttcaa ctcatccaca acataatcct aatgaaaatg     960
aaattctagt agctgacact tatgaccaaa gtcaatctcc aatggccaaa gcacatgaaa    1020
caagcagcta taccctgat aagtcatctt ttaatttagc tacagttgtt gctgaaacac    1080
ttggacttgg tgttcaagaa gaatctgaaa ctcaaggtcc catgagcccc cttggtgatg    1140
agctctacca ctgtctggaa ggaaatcaca agaaacagcc ttttgaggaa tctacaagaa    1200
atactgaaga tagtttaaga ttttcagatt ctacttcaaa gactcctcct caagaagaat    1260
tacctactcg agtgtcatct cctgtatttg gagctacctc tagtatcaaa agtggtttag    1320
atttgaatac aagtttgtcc ccttctcttt tacagcctgg gaaaaaaaaa catctgaaaa    1380
cactcccttt tagcaacact tgtatatcta gattagaaaa aactagatca aaatctgaag    1440
atagtgccct tttcacacat cacagtcttg ggtctgaagt gaacaagatc attatccagt    1500
catctaataa acagatactt ataaataaaa atataagtga atccctaggt gaacagaata    1560
ggactgagta cggtaaagat tctaacactg ataaacattt ggagcccctg aaatcattgg    1620
gaggccgaac atccaaaagg aagaaaactg aggaagaaag tgaacatgaa gtaagctgcc    1680
```

-continued

```
cccaagcttc ttttgataaa gaaaatgctt tcccttttcc aatgggataat cagttttcca   1740 tgaatggaga ctgtgtgatg gataaacctc tggatctgtc tgatcgattt tcagctattc   1800
agcgtcaaga gaaaagccaa ggaagtgaga cttctaaaaa caaatttagg caagtgactc   1860
tttatgaggc tttgaagacc attccaaagg gcttttcctc aagccgtaag gcctcagatg   1920
gcaactgcac gttgcccaaa gattccccag gggagccctg ttcacaggaa tgcatcatcc   1980
ttcagccctt gaataaatgc tctccagaca ataaccatc attacaaata aagaagaaa    2040 atgctgtctt taaaattcct ctacgtccac gtgaaagttt ggagactgag aatgttttag   2100
atgacataaa gagtgctggt tctcatgagc caataaaaat acaaaccagg tcagaccatg   2160
gaggatgtga acttgcatca gttcttcagt taaatccatg tagaactggt aaaataaagt   2220
ctctacaaaa caaccaagat gtatcctttg aaaatatcca gtggagtata gatccgggag   2280
cagacctttc tcagtataaa atggatgtta ctgtaataga tacaaaggat ggcagtcagt   2340
caaaattagg aggagagaca gtggacatgg actgtacatt ggttagtgaa accgttctct   2400
taaaaatgaa gaagcaagag cagaagggag aaaaagttc aaatgaagaa agaaaaatga    2460
atgatagctt ggaagatatg tttgatcgga caacacatga gagtatgaa tcctgtttgg    2520 cagacagttt ctcccaagca gcagatgaag aggaggaatt gtctactgcc acaaagaaac   2580
tacacactca tggtgataaa caagacaaag tcaagcagaa agcgtttgtg gagccgtatt   2640
ttaaaggtga tgaaagagag actagcttgc aaaattttcc tcatattgag gtggttcgga   2700
aaaaagagga gagaagaaaa ctgcttgggc acacgtgtaa ggaatgtgaa atttattatg   2760
cagatatgcc agcagaagaa agagaaaaga aattggcttc ctgctcaaga caccgattcc   2820
gctacattcc acccaacaca ccagagaatt tttgggaagt tggttttcct tccactcaga   2880
cttgtatgga aagaggttat attaaggaag atcttgatcc ttgtcctcgt ccaaaaagac   2940
gtcagcctta caacgcaata ttttctccaa aggcaagga gcagaagaca tagacgttga    3000
aacagaaaca gaaggatgaa ggacagtttt ttccttctta gttatttata gttaaagttg   3060
gtactaaaca ttgattttt tgatcttctg taaatggatt tataaatcag ttttctattg    3120
aaaatgtttg tgatatttg cttttgcacc tttaaaacaa taaggcgctt tcattttgca    3180
ctctaactta agagttttta ctttatgtag tgatacctaa tacaattttg aaaatacaaa   3240
aaaaaaa                                                              3247
```

<210> SEQ ID NO 2
<211> LENGTH: 897
<212> TYPE: PRT
<213> ORGANISM: Homo sapiens

<400> SEQUENCE: 2

```
Met Asn Ile Leu Gly Ser Ser Cys Gly Ser Pro Asn Ser Ala Asp Thr
1               5                   10                  15

Ser Ser Asp Phe Lys Asp Leu Trp Thr Lys Leu Lys Glu Cys His Asp
                20                  25                  30

Arg Glu Val Gln Gly Leu Gln Val Lys Val Thr Lys Leu Lys Gln Glu
            35                  40                  45

Arg Ile Leu Asp Ala Gln Arg Leu Glu Glu Phe Phe Thr Lys Asn Gln
        50                  55                  60

Gln Leu Arg Glu Gln Gln Lys Val Leu His Glu Thr Ile Lys Val Leu
    65                  70                  75                  80

Glu Asp Arg Leu Arg Ala Gly Leu Cys Asp Arg Cys Ala Val Thr Glu
                85                  90                  95
```

-continued

```
Glu His Met Arg Lys Lys Gln Gln Glu Phe Glu Asn Ile Arg Gln Gln
            100                 105                 110

Asn Leu Lys Leu Ile Thr Glu Leu Met Asn Glu Arg Asn Thr Leu Gln
            115                 120                 125

Glu Glu Asn Lys Lys Leu Ser Glu Gln Leu Gln Gln Lys Ile Glu Asn
            130                 135                 140

Asp Gln Gln His Gln Ala Ala Glu Leu Glu Cys Glu Glu Asp Val Ile
145                 150                 155                 160

Pro Asp Ser Pro Ile Thr Ala Phe Ser Phe Ser Gly Val Asn Arg Leu
                    165                 170                 175

Arg Arg Lys Glu Asn Pro His Val Arg Tyr Ile Glu Gln Thr His Thr
                    180                 185                 190

Lys Leu Glu His Ser Val Cys Ala Asn Glu Met Arg Lys Val Ser Lys
            195                 200                 205

Ser Ser Thr His Pro Gln His Asn Pro Asn Glu Asn Glu Ile Leu Val
            210                 215                 220

Ala Asp Thr Tyr Asp Gln Ser Gln Ser Pro Met Ala Lys Ala His Gly
225                 230                 235                 240

Thr Ser Ser Tyr Thr Pro Asp Lys Ser Ser Phe Asn Leu Ala Thr Val
                    245                 250                 255

Val Ala Glu Thr Leu Gly Leu Gly Val Gln Glu Glu Ser Glu Thr Gln
            260                 265                 270

Gly Pro Met Ser Pro Leu Gly Asp Glu Leu Tyr His Cys Leu Glu Gly
            275                 280                 285

Asn His Lys Lys Gln Pro Phe Glu Glu Ser Thr Arg Asn Thr Glu Asp
            290                 295                 300

Ser Leu Arg Phe Ser Asp Ser Thr Ser Lys Thr Pro Pro Gln Glu Glu
305                 310                 315                 320

Leu Pro Thr Arg Val Ser Ser Pro Val Phe Gly Ala Thr Ser Ser Ile
                    325                 330                 335

Lys Ser Gly Leu Asp Leu Asn Thr Ser Leu Ser Pro Ser Leu Leu Gln
            340                 345                 350

Pro Gly Lys Lys Lys His Leu Lys Thr Leu Pro Phe Ser Asn Thr Cys
            355                 360                 365

Ile Ser Arg Leu Glu Lys Thr Arg Ser Lys Ser Glu Asp Ser Ala Leu
            370                 375                 380

Phe Thr His His Ser Leu Gly Ser Glu Val Asn Lys Ile Ile Ile Gln
385                 390                 395                 400

Ser Ser Asn Lys Gln Ile Leu Ile Asn Lys Asn Ile Ser Glu Ser Leu
                    405                 410                 415

Gly Glu Gln Asn Arg Thr Glu Tyr Gly Lys Asp Ser Asn Thr Asp Lys
            420                 425                 430

His Leu Glu Pro Leu Lys Ser Leu Gly Gly Arg Thr Ser Lys Arg Lys
            435                 440                 445

Lys Thr Glu Glu Glu Ser Glu His Glu Val Ser Cys Pro Gln Ala Ser
            450                 455                 460

Phe Asp Lys Glu Asn Ala Phe Pro Phe Pro Met Asp Asn Gln Phe Ser
465                 470                 475                 480

Met Asn Gly Asp Cys Val Met Asp Lys Pro Leu Asp Leu Ser Asp Arg
                    485                 490                 495

Phe Ser Ala Ile Gln Arg Gln Glu Lys Ser Gln Gly Ser Glu Thr Ser
            500                 505                 510
```

-continued

```
Lys Asn Lys Phe Arg Gln Val Thr Leu Tyr Glu Ala Leu Lys Thr Ile
            515                 520                 525
Pro Lys Gly Phe Ser Ser Arg Lys Ala Ser Asp Gly Asn Cys Thr
    530                 535                 540
Leu Pro Lys Asp Ser Pro Gly Glu Pro Cys Ser Gln Glu Cys Ile Ile
545                 550                 555                 560
Leu Gln Pro Leu Asn Lys Cys Ser Pro Asp Asn Lys Pro Ser Leu Gln
                565                 570                 575
Ile Lys Glu Glu Asn Ala Val Phe Lys Ile Pro Leu Arg Pro Arg Glu
            580                 585                 590
Ser Leu Glu Thr Glu Asn Val Leu Asp Asp Ile Lys Ser Ala Gly Ser
        595                 600                 605
His Glu Pro Ile Lys Ile Gln Thr Arg Ser Asp His Gly Gly Cys Glu
    610                 615                 620
Leu Ala Ser Val Leu Gln Leu Asn Pro Cys Arg Thr Gly Lys Ile Lys
625                 630                 635                 640
Ser Leu Gln Asn Asn Gln Asp Val Ser Phe Glu Asn Ile Gln Trp Ser
                645                 650                 655
Ile Asp Pro Gly Ala Asp Leu Ser Gln Tyr Lys Met Asp Val Thr Val
            660                 665                 670
Ile Asp Thr Lys Asp Gly Ser Gln Ser Lys Leu Gly Gly Glu Thr Val
        675                 680                 685
Asp Met Asp Cys Thr Leu Val Ser Glu Thr Val Leu Leu Lys Met Lys
    690                 695                 700
Lys Gln Glu Gln Lys Gly Glu Lys Ser Ser Asn Glu Glu Arg Lys Met
705                 710                 715                 720
Asn Asp Ser Leu Glu Asp Met Phe Asp Arg Thr Thr His Glu Glu Tyr
                725                 730                 735
Glu Ser Cys Leu Ala Asp Ser Phe Ser Gln Ala Ala Asp Glu Glu Glu
            740                 745                 750
Glu Leu Ser Thr Ala Thr Lys Lys Leu His Thr His Gly Asp Lys Gln
        755                 760                 765
Asp Lys Val Lys Gln Lys Ala Phe Val Glu Pro Tyr Phe Lys Gly Asp
    770                 775                 780
Glu Arg Glu Thr Ser Leu Gln Asn Phe Pro His Ile Glu Val Val Arg
785                 790                 795                 800
Lys Lys Glu Glu Arg Arg Lys Leu Leu Gly His Thr Cys Lys Glu Cys
                805                 810                 815
Glu Ile Tyr Tyr Ala Asp Met Pro Ala Glu Glu Arg Glu Lys Lys Leu
            820                 825                 830
Ala Ser Cys Ser Arg His Arg Phe Arg Tyr Ile Pro Pro Asn Thr Pro
        835                 840                 845
Glu Asn Phe Trp Glu Val Gly Phe Pro Ser Thr Gln Thr Cys Met Glu
    850                 855                 860
Arg Gly Tyr Ile Lys Glu Asp Leu Asp Pro Cys Pro Arg Pro Lys Arg
865                 870                 875                 880
Arg Gln Pro Tyr Asn Ala Ile Phe Ser Pro Lys Gly Lys Glu Gln Lys
                885                 890                 895
Thr

<210> SEQ ID NO 3
<211> LENGTH: 2694
<212> TYPE: DNA
<213> ORGANISM: Homo sapiens
```

<400> SEQUENCE: 3

```
atgaacatct tgggaagcag ctgtggaagc cctaactctg cagatacatc tagtgacttt      60
aaggaccttt ggacaaaact aaaagaatgt catgatagag aagtacaagg tttacaagta     120
aaagtaacca agctaaaaca ggaacgaatc ttagatgcac aaagactaga agaattcttc     180
accaaaaatc aacagctgag ggaacagcag aaagtccttc atgaaaccat taagttttta     240
gaagatcggt taagagcagg cttatgtgat cgctgtgcag taactgaaga acatatgcgg     300
aaaaacagc aagagtttga aaatatccgg cagcagaatc ttaaacttat tacagaactt      360
atgaatgaaa ggaatactct acaggaagaa aataaaaagc tttctgaaca actccagcag     420
aaaattgaga tgatcaaca gcatcaagca gctgagcttg aatgtgagga agacgttatt      480
ccagattcac cgataacagc cttctcattt tctggcgtta accggctacg aagaaaggag     540
aaccccccatg tccgatacat agaacaaaca catactaaat ggagcactc tgtgtgtgca     600
aatgaaatga gaaaagtttc caagtcttca actcatccac aacataatcc taatgaaaat     660
gaaattctag tagctgacac ttatgaccaa agtcaatctc caatggccaa agcacatgga     720
acaagcagct atacccctga taagtcatct tttaatttag ctacagttgt tgctgaaaca     780
cttggacttg gtgttcaaga agaatctgaa actcaaggtc ccatgagccc ccttggtgat     840
gagctctacc actgtctgga aggaaatcac aagaaacagc cttttgagga atctacaaga     900
aatactgaag atagtttaag attttcagat tctacttcaa agactcctcc tcaagaagaa     960
ttacctactc gagtgtcatc tcctgtattt ggagctacct ctagtatcaa aagtggttta    1020
gatttgaata caagtttgtc cccttctctt ttacagcctg ggaaaaaaaa acatctgaaa    1080
acactcccctt ttagcaacac ttgtatatct agattagaaa aaactagatc aaaatctgaa    1140
gatagtgccc ttttcacaca tcacagtctt gggtctgaag tgaacaagat cattatccag    1200
tcatctaata aacagatact tataaataaa aatataagtg aatccctagg tgaacagaat    1260
aggactgagt acggtaaaga ttctaacact gataaacatt tggagcccct gaaatcattg    1320
ggaggccgaa catccaaaag gaagaaaact gaggaagaaa gtgaacatga agtaagctgc    1380
ccccaagctt cttttgataa agaaaatgct ttccctttc caatggataa tcagttttcc     1440
atgaatggag actgtgtgat ggataaacct ctggatctgt ctgatcgatt ttcagctatt    1500
cagcgtcaag agaaaagcca aggaagtgag acttctaaaa acaaatttag gcaagtgact    1560
ctttatgagg ctttgaagac cattccaaag ggcttttcct caagccgtaa ggcctcagat    1620
ggcaactgca cgttgcccaa agattcccca ggggagccct gttcacagga atgcatcatc    1680
cttcagccct gaataaaatg ctctccagac aataaaccat cattacaaat aaaagaagaa    1740
aatgctgtct ttaaaattcc tctacgtcca cgtgaaagtt tggagactga aatgttttta    1800
gatgacataa agagtgctgg ttctcatgag ccaataaaaa tacaaaccag gtcagaccat    1860
ggaggatgtg aacttgcatc agttcttcag ttaaatccat gtagaactgg taaaataaag    1920
tctctacaaa acaaccaaga tgtatccttt gaaaatatcc agtggagtat agatccggga    1980
gcagaccttt ctcagtataa aatggatgtt actgtaatag atacaaagga tggcagtcag    2040
tcaaaattag gaggagagac agtggacatg gactgtacat tggttagtga aaccgttctc    2100
ttaaaaatga agaagcaaga gcagaaggga gaaaaagtt caaatgaaga aagaaaaatg    2160
aatgatagct tggaagatat gtttgatcgg acaacacatg aagagtatga atcctgtttg    2220
gcagacagtt tctcccaagc agcagatgaa gaggaggaat tgtctactgc cacaaagaaa    2280
ctacacactc atggtgataa acaagacaaa gtcaagcaga aagcgtttgt ggagccgtat    2340
```

-continued

| | |
|---|---|
| tttaaaggtg atgaaagaga gactagcttg caaaattttc ctcatattga ggtggttcgg | 2400 |
| aaaaaagagg agagaagaaa actgcttggg cacacgtgta aggaatgtga aatttattat | 2460 |
| gcagatatgc cagcagaaga aagagaaaag aaattggctt cctgctcaag acaccgattc | 2520 |
| cgctacattc cacccaacac accagagaat ttttgggaag ttggttttcc ttccactcag | 2580 |
| acttgtatgg aaagaggtta tattaaggaa gatcttgatc cttgtcctcg tccaaaaaga | 2640 |
| cgtcagcctt acaacgcaat attttctcca aaaggcaagg agcagaagac atag | 2694 |

<210> SEQ ID NO 4
<211> LENGTH: 2694
<212> TYPE: DNA
<213> ORGANISM: Homo sapiens

<400> SEQUENCE: 4

| | |
|---|---|
| ctatgtcttc tgctccttgc cttttggaga aaatattgcg ttgtaaggct gacgtcttt | 60 |
| tggacgagga caaggatcaa gatcttcctt aatataacct ctttccatac aagtctgagt | 120 |
| ggaaggaaaa ccaacttccc aaaaattctc tggtgtgttg ggtggaatgt agcggaatcg | 180 |
| gtgtcttgag caggaagcca atttcttttc tctttcttct gctggcatat ctgcataata | 240 |
| aatttcacat tccttacacg tgtgcccaag cagttttctt ctctcctctt ttttccgaac | 300 |
| cacctcaata tgaggaaaat tttgcaagct agtctctctt tcatcacctt taaaatacgg | 360 |
| ctccacaaac gctttctgct tgactttgtc ttgtttatca ccatgagtgt gtagtttctt | 420 |
| tgtggcagta gacaattcct cctcttcatc tgctgcttgg gagaaactgt ctgccaaaca | 480 |
| ggattcatac tcttcatgtg ttgtccgatc aaacatatct tccaagctat cattcatttt | 540 |
| tctttcttca tttgaacttt tttctccctt ctgctcttgc ttcttcattt ttaagagaac | 600 |
| ggtttcacta accaatgtac agtccatgtc cactgtctct cctcctaatt ttgactgact | 660 |
| gccatccttt gtatctatta cagtaacatc cattttatac tgagaaaggt ctgctcccgg | 720 |
| atctatactc cactggatat tttcaaagga tacatcttgg ttgttttgta gagactttat | 780 |
| tttaccagtt ctacatggat ttaactgaag aactgatgca agttcacatc ctccatggtc | 840 |
| tgacctggtt tgtattttta ttggctcatg agaaccagca ctctttatgt catctaaaac | 900 |
| attctcagtc tccaaacttt cacgtggacg tagaggaatt ttaaagacag cattttcttc | 960 |
| ttttatttgt aatgatggtt tattgtctgg agagcattta ttcaagggct gaaggatgat | 1020 |
| gcattcctgt gaacagggct cccctgggga atctttgggc aacgtgcagt tgccatctga | 1080 |
| ggccttacgg cttgaggaaa agccctttgg aatggtcttc aaagcctcat aaagagtcac | 1140 |
| ttgcctaaat ttgttttag aagtctcact tccttggctt ttctcttgac gctgaatagc | 1200 |
| tgaaaatcga tcagacagat ccagaggttt atccatcaca cagtctccat tcatggaaaa | 1260 |
| ctgattatcc attggaaaag ggaaagcatt ttctttatca aaagaagctt gggggcagct | 1320 |
| tacttcatgt tcactttctt cctcagtttt cttcctttg gatgttcggc ctcccaatga | 1380 |
| tttcagggc tccaaatgtt tatcagtgtt agaatcttta ccgtactcag tcctattctg | 1440 |
| ttcacctagg gattcactta tatttttatt tataagtatc tgtttattag atgactggat | 1500 |
| aatgatcttg ttcacttcag acccaagact gtgatgtgtg aaaagggcac tatcttcaga | 1560 |
| ttttgatcta gttttttcta atctagatat acaagtgttg ctaaagggga gtgttttcag | 1620 |
| atgttttttt ttcccaggct gtaaaagaga aggggacaaa cttgtattca aatctaaacc | 1680 |
| acttttgata ctagaggtag ctccaaatac aggagatgac actcgagtag gtaattcttc | 1740 |
| ttgaggagga gtctttgaag tagaatctga aaatcttaaa ctatcttcag tatttcttgt | 1800 |

-continued

```
agattcctca aaaggctgtt tcttgtgatt tccttccaga cagtggtaga gctcatcacc    1860 aaggggctc atgggacctt gagtttcaga ttcttcttga acaccaagtc caagtgtttc    1920
agcaacaact gtagctaaat taaaagatga cttatcaggg gtatagctgc ttgttccatg    1980
tgctttggcc attggagatt gactttggtc ataagtgtca gctactagaa tttcattttc    2040
attaggatta tgttgtggat gagttgaaga cttggaaact tttctcattt catttgcaca    2100
cacagagtgc tccaatttag tatgtgtttg ttctatgtat cggacatggg ggttctcctt    2160
tcttcgtagc cggttaacgc cagaaaatga gaaggctgtt atcggtgaat ctggaataac    2220
gtcttcctca cattcaagct cagctgcttg atgctgttga tcattctcaa ttttctgctg    2280
gagttgttca gaaagctttt tattttcttc ctgtagagta ttcctttcat tcataagttc    2340
tgtaataagt ttaagattct gctgccggat attttcaaac tcttgctgtt ttttccgcat    2400
atgttcttca gttactgcac agcgatcaca taagcctgct cttaaccgat cttctaaaac    2460
tttaatggtt tcatgaagga ctttctgctg ttccctcagc tgttgatttt tggtgaagaa    2520
ttcttctagt ctttgtgcat ctaagattcg ttcctgtttt agcttggtta cttttacttg    2580
taaaccttgt acttctctat catgacattc ttttagtttt gtccaaaggt ccttaaagtc    2640
actagatgta tctgcagagt tagggcttcc acagctgctt cccaagatgt tcat          2694
```

<210> SEQ ID NO 5
<211> LENGTH: 22
<212> TYPE: PRT
<213> ORGANISM: Adenovirus type 2

<400> SEQUENCE: 5

Cys Ile Glu Asp Leu Leu His Glu Pro Gly Gln Pro Leu Asp Leu Ser
  1               5                  10                  15

Cys Lys Arg Pro Arg Pro
            20

<210> SEQ ID NO 6
<211> LENGTH: 27
<212> TYPE: PRT
<213> ORGANISM: Adenovirus type 12

<400> SEQUENCE: 6

Ser Ile Leu Asp Leu Ile Gln Glu Glu Glu Arg Glu Gln Thr Val Pro
  1               5                  10                  15

Val Asp Leu Ser Val Lys Arg Pro Arg Cys Asn
            20                  25

<210> SEQ ID NO 7
<211> LENGTH: 23
<212> TYPE: PRT
<213> ORGANISM: Adenovirus type 7

<400> SEQUENCE: 7

Lys Leu Glu Asp Leu Leu Glu Gly Gly Asp Gly Pro Leu Asp Leu Ser
  1               5                  10                  15

Thr Arg Lys Leu Pro Arg Gln
            20

<210> SEQ ID NO 8
<211> LENGTH: 23
<212> TYPE: PRT
<213> ORGANISM: Adenovirus type 4

```
<400> SEQUENCE: 8

Cys Leu Asp Asp Leu Leu Gln Gly Gly Asp Glu Pro Leu Asp Leu Cys
1               5                   10                  15

Thr Arg Lys Arg Pro Arg His
            20

<210> SEQ ID NO 9
<211> LENGTH: 25
<212> TYPE: PRT
<213> ORGANISM: Adenovirus type 40

<400> SEQUENCE: 9

Cys Ile Glu Asp Leu Leu Glu Glu Asp Pro Thr Asp Glu Pro Leu Asn
1               5                   10                  15

Leu Ser Leu Lys Arg Pro Lys Cys Ser
            20                  25

<210> SEQ ID NO 10
<211> LENGTH: 25
<212> TYPE: PRT
<213> ORGANISM: Simian Adenovirus type 7

<400> SEQUENCE: 10

Ser Leu His Asp Leu Ile Glu Glu Val Glu Gln Thr Val Pro Leu Asp
1               5                   10                  15

Leu Ser Leu Lys Arg Ser Arg Ser Asn
            20                  25

<210> SEQ ID NO 11
<211> LENGTH: 27
<212> TYPE: PRT
<213> ORGANISM: Homo sapiens

<400> SEQUENCE: 11

Met Asp Asn Gln Phe Ser Met Asn Gly Asp Cys Val Met Asp Lys Pro
1               5                   10                  15

Leu Asp Leu Ser Asp Arg Phe Ser Ala Ile Gln
            20                  25

<210> SEQ ID NO 12
<211> LENGTH: 5
<212> TYPE: PRT
<213> ORGANISM: Homo sapiens

<400> SEQUENCE: 12

Pro Leu Asp Leu Ser
1               5
```